US009309501B2

(12) United States Patent
Liu et al.

(10) Patent No.: US 9,309,501 B2
(45) Date of Patent: Apr. 12, 2016

(54) ISOLATED DNA POLYMERASES, KITS AND APPLICATIONS THEREOF

(71) Applicant: Industrial Technology Research Institute, Hsinchu (TW)

(72) Inventors: Tseng-Huang Liu, Kaohsiung (TW); Pei-Shin Jiang, Hsinchu (TW); Chih-Lung Lin, Taichung (TW); Su-Jan Lee, Taipei (TW); Chao-Hung Kao, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 14/138,155

(22) Filed: Dec. 23, 2013

(65) Prior Publication Data

US 2014/0186894 A1 Jul. 3, 2014

Related U.S. Application Data

(60) Provisional application No. 61/745,649, filed on Dec. 24, 2012.

(51) Int. Cl.
*C12N 9/12* (2006.01)

(52) U.S. Cl.
CPC .................... *C12N 9/1252* (2013.01)

(58) Field of Classification Search
None
See application file for complete search history.

(56) References Cited

U.S. PATENT DOCUMENTS

| 5,436,326 | A | * | 7/1995 | Ishino et al. ............. 536/23.2 |
| 5,814,506 | A | | 9/1998 | Kong et al. |
| 5,830,714 | A | | 11/1998 | Swaminathan et al. |
| 7,049,101 | B1 | | 5/2006 | Callen et al. |
| 2008/0254525 | A1 | * | 10/2008 | Zheng et al. ............. 435/193 |
| 2008/0311626 | A1 | | 12/2008 | Hjorleifsdottir et al. |
| 2012/0115145 | A1 | | 5/2012 | Fu |
| 2012/0115188 | A1 | | 5/2012 | Faurholm et al. |

FOREIGN PATENT DOCUMENTS

| CN | 101134974 | | 3/2008 |
| CN | 102414315 | | 4/2012 |
| TW | 588050 | | 5/2004 |
| TW | 528802 | | 4/2013 |
| WO | WO 2013/033528 | * | 3/2013 |

OTHER PUBLICATIONS

P00581; last viewed on Apr. 14, 2015.*
Branden and Tooze, Introduction to Protein Structure (1999), 2nd edition, Garland Science Publisher, pp. 3-12.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*

(Continued)

*Primary Examiner* — Alexander Kim
(74) *Attorney, Agent, or Firm* — Jianq Chyun IP Office

(57) ABSTRACT

Isolated DNA polymerase and the mutant DNA polymerases thereof are provided. The DNA polymerases have good thermostability.

7 Claims, 16 Drawing Sheets

(56) References Cited

OTHER PUBLICATIONS

Wacey et al., Disentangling the perturbational effects of amino acid substitutions in the DNA-binding domain of p53., Hum Genet, 1999, vol. 104, pp. 15-22.*
EMBL DB ID: Q5KWC1_GEOKA, Feb. 1, 2005, pp. 1-9.
"Office Action of Taiwan Counterpart Application", issued on Dec. 23, 2014, p. 1-p. 7, in which the listed reference was.
Kiefer et al., "Crystal structure of a thermostable Bacillus DNA polymerase I large fragment at 2.1 Å resolution," Structure, Jan. 15, 1997, pp. 95-108, vol. 5, No. 1.
Pavlov et al., "Cooperation between Catalytic and DNA Binding Domains Enhances Thermostability and Supports DNA Synthesis at Higher Temperatures by Thermostable DNA Polymerases," Biochemistry, Feb. 8, 2012, pp. 2032-2043, vol. 51.
Ong et al., "Directed Evolution of DNA Polymerase, RNA Polymerase and Reverse Transcriptase Activity in a Single Polypeptide," Journal of Molecular Biology, Aug. 18, 2006, pp. 537-550, vol. 361.
Henry and Romesberg, "The evolution of DNA polymerases with novel activities," Current Opinion in Biotechnology, Jul. 11, 2005, pp. 370-377, vol. 16.
Holmberg et al, "Directed evolution of novel polymerases," Biomolecular Engineering, Jun. 2005, pp. 39-49, vol. 22.
Lu et al., "Large fragment of DNA polymerase I from Bacillus stearothermophilus (Bst polymerase) is stable at ambient temperature", Biotechniques, Oct. 1991, pp. 464-466, vol. 11, No. 4.
Goto et al., "Colorimetric detection of loopmediated isothermal amplification reaction by using hydroxy naphthol blue," Biotechniques, Mar. 2009, pp. 167-172, vol. 46.
Parida et al., "Loop mediated isothermal amplification (LAMP): a new generation of innovative gene amplification technique; perspectives in clinical diagnosis of infectious diseases," Reviews in Medical Virology, Aug. 20, 2008, pp. 407-421.
Kim et al., "Improved thermostability and PCR efficiency of Thermococcus celericrescens DNA polymerase via site-directed mutagenesis," Journal of Biotechnology, Jun. 23, 2011, pp. 156-163, vol. 155.
Aliotta et al., "Thermostable Bst DNA polymerase I lacks a 3'-> 5' proofreading exonuclease activity," Genetic Analysis: Biomolecular Engineering, Mar. 1996, pp. 185-195, vol. 12.
Muhd Sakaff, et al., "Geobacillus thermoleovorans CCB_US3_UF5," NCBI Protein Database, retrieved date: Aug. 5, 2015.
"Office Action of China Counterpart Application," issued on Jul. 3, 2015, p. 1-p. 6, in which the listed references were cited.

* cited by examiner

> *Geobacillus kaustophilus* BCRC11223    -SEQ ID NO.2

MRLKKKLVLIDGSSVAYRAFFALPLLHNDKGIHTNAVYGFTMMLNKILAEEEPTHMLVAFDAGKTT
FRHEAFQEYKGGRQQTPPELSEQFPLLRELLRAYRIPAYELENYEADDIIGTLAARAEQEGFEVKVIS
GDRDLTQLASPHVTVDITKKGITDIEPYTPETVREKYGLTPEQIVDLKGLMGDKSDNIPGVPGIGEKT
AVKLLRQFGTVENVLASIDEIKGEKLKETLRQHREMALLSKKLAAIRRDAPVELSLDDIVYQGEDRE
KVVALFKELGFQSFLEKMESPSSEEEKPLAKMAFTLADRVTEEMLADKAALVVEVVEENYHDAPIV
GIAVVNEHGRFFLRPETALADPQFVAWLGDETKKKSMFDSKRAAVALKWKGIELCGVSFDLLLAAY
LLDPAQGVDDVAAAAKMKQYEAVRPDEAVYGKGAKRAVPDEPVLAEHLVRKAAAIWELERPFLDE
LRRNEQDRLLVELEQPLSSILAEMEFAGVKVDTKRLEQMGKELAEQLGTVEQRIYELAGQEFNINSP
KQLGVILFEKLQLPVLKKTKTGYSTSADVLEKLAPYHEIVENILHYRQLGKLQSTYIEGLLKVVRPD
TKKVHTIFNQALTQTGRLSSTEPNLQNIPIRLEEGRKIRQAFVPSESDWLIFAADYSQIELRVLAHIAE
DDNLMEAFRRDLDIHTKTAMDIFQVSEDEVTPNMRRQAKAVNFGIVYGISDYGLAQNLNISRKEAA
EFIERYFESFPGVKRYMENIVQEAKQKGYVTTLLHRRRYLPDITSRNFNVRSFAERMAMNTPIQGSA
ADIKKAMIDLNARLKEERLQARLLLQVHDELILEAPKEEMERLCRLVPEVMEQAVTLRVPLKVDY
HYGSTWYDAK

[DNA polymerase I large fragment]

> *Geobacillus stearothermophilus* - Strain 10    -SEQ ID NO.1

MRLKKKLVLIDGSSVAYRAFFALPLLHNDKGIHTNAVYGFTMMLNKILAEEEPTHMLVAF
DAGKTTFRHEAFQEYKGGRQQTPPELSEQFPLLRELLRAYRIPAYELENYEADDIIGTLA
ARAEQEGFEMKVISGDRDLTQLASPHVTVDITKKGITDIEPYTPETVREKYGLTPEQIVD
LKGLMGDKSDNIPGVPGIGE KTAVKLLRQF GTVENVLASI DEIKGEKLKE TLRQHREMAL
LSKKLAAIRRD APVELSLDD IAYQGEDREK VVALFKELGF QSFLEKMESP SSEEEKPLAK
MAFTLADRVTEEMLADKAAL VVEVVEENYH DAPIVGIAVV NEHGRFFLRP ETALADPQFV
AWLGDETKKKSMFDSKRAAV ALKWKGIELC GVSFDLLLAA YLLDPAQGVD DVAAAAKMKQ
YEAVRPDEAVYGKGAKRAVP DEPVLAEHLV RKAAAIWALE RPFLDELRRN EQDRLLVELE
QPLSSILAEM EFAGVKVDTK RLEQMGEELA EQLRTVEQRI YELAGQEFNI NSPKQLGVIL
FEKLQLPVLK KTKTGYSTSA DVLEKLAPYH EIVENILHYR QLGKLQSTYI EGLLKVVRPD
TKKVHTIFNQ ALTQTGRLSS TEPNLQNIPI RLEEGRKIRQ AFVPSESDWL IFAADYSQIE
LRVLAHIAED DNLMEAFRRD LDIHTKTAMD IFQVSEDEVT PNMRRQAKAV NFGIVYGISD
YGLAQNLNIS RKEAAEFIER YFESFPGVKR YMENIVQEAK QKGYVTTLLH RRRYLPDITS
RNFNVRSFAE RMAMNTPIQG SAADIKKAM IDLNARLKEE RLQARLLLQV HDELILEAPK
EEMERLCRLV PEVMEQAVTL RVPLKVDYHY GSTWYDAK

[DNA polymerase I large fragment]

FIG. 2A

1XWL-SEQ ID NO.7
BCRC11223-SEQ ID NO.2
Strain10-SEQ ID NO.1

```
                    E309~A313                                    P348
1XWL       --------ARMAFTLADRVTEEMLADKAALVVEVVEENYHDAPIVGIAVVNEHGRFFLREE  53
BCRC11223  SEEEKPLARMAFTLADRVTEEMLADKAALVVEVVEENYHDAPIVGIAVVNEHGRFFLREE  60
Strain10   SEEEKPLARMAFTLADRVTEEMLADKAALVVEVVEENYHDAPIVGIAVVNEHGRFFLREE  60
                   ********************************************************

V358~T365                           A404~Q405
1XWL       TALADPQFVAMLGDETKKKSMFDSKRAAVALKWKGIELCGVSFDLLLAAYLLDPAQGVDD  113
BCRC11223  TALADPQFVAMLGDETKKKSMFDSKRAAVALKWKGIELCGVSFDLLLAAYLLDPAQGVDD  120
Strain10   TALADPQFVAMLGDETKKKSMFDSKRAAVALKWKGIELCGVSFDLLLAAYLLDPAQGVDD  120
           ************************************************************

P424~E445
1XWL       VAAAAKMKQYEAVRPDEAVYGRGAKRAVPDEPVLAEHLVRKAAAIWELERPFLDELRRNE  173
BCRC11223  VAAAAKMKQYEAVRPDEAVYGRGAKRAVPDEPVLAEHLVRKAAAIWELERPFLDELRRNE  180
Strain10   VAAAAKMKQYEAVRPDEAVYGKGAKRAVPDEPVLAEHLVRKAAAIWALERPFLDELRRNE  180
           ****************************************************.*******

1XWL       QDRLLVELEQPLSSILAEMEFAGVKVDTKRLEQMGRELAEQHGFVEQRIYELAGQEFNIN  233
BCRC11223  QDRLLVELEQPLSSILAEMEFAGVKVDTKRLEQMGRELAEQHGFVEQRIYELAGQEFNIN  240
Strain10   QDRLLVELEQPLSSILAEMEFAGVKVDTKRLEQMGEELAEQURFVEQRIYELAGQEFNIN  240
           ***********************************  *****  ***************

1XWL       SPKQLGVILFEKLQLPVLKKTKTGYSTSADVLEKLAPYHEIVENILHYRQLGKLQSTYIE  293
BCRC11223  SPKQLGVILFEKLQLPVLKKTKTGYSTSADVLEKLAPYHEIVENILHYRQLGKLQSTYIE  300
Strain10   SPKQLGVILFERLQLPVLRKTKTGYSTSADVLEKLAPYHEIVENILHYRQLGKIQSTYIE  300
           ***********************************************************

1XWL       GLLKVVRPDTKKVHTIFNQALTQTGRLSSTEPNLQNIPIRLEEGRKIRQAFVPSESDWLI  353
BCRC11223  GLLKVVRPDTKKVHTIFNQALTQTGRLSSTEPNLQNIPIRLEEGRKIRQAFVPSESDWLI  360
Strain10   GLLKVVRPDTKKVHTIFNQALTQTGRLSSTEPNLQNIPIRLEEGRKIRQAFVPSESDWLI  360
           ************************************************************

1XWL       FAADYSQIELRVLAHIAEDDNLMEAFRRDLDIHTKTAMDIFQVSEDEVTPNMRRQAKAVN  413
BCRC11223  FAADYSQIELRVLAHIAEDDNLMEAFRRDLDIHTKTAMDIFQVSEDEVTPNMRRQAKAVN  420
Strain10   FAADYSQIELRVLAHIAEDDNLMEAFRRDLDIHTKTAMDIFQVSEDEVTPNMRRQAKAVN  420
           ************************************************************

1XWL       FGIVYGISDYGLAQNLNISRKEAAEFIERYFESFPGVKRYMENIVQEAKQKGYVTTLLHR  473
BCRC11223  FGIVYGISDYGLAQNLNISRKEAAEFIERYFESFPGVKRYMENIVQEAKQKGYVTTLLHR  480
Strain10   FGIVYGISDYGLAQNLNISRKEAAEFIERYFESFPGVKRYMENIVQEAKQKGYVTTLLHR  480
           ************************************************************

1XWL       RRYLPDITSRNFNVRSFAERMAMNTPIQGSAADIIKKAMIDLNARLKEERLQAHLLLQVH  533
BCRC11223  RRYLPDITSRNFNVRSFAERMAMNTPIQGSAADIIKKAMIDLNARLKEERLQARLLLQVH  540
Strain10   RRYLPDITSRNFNVRSFAERMAMNTPIQGSAADIIKKAMIDLNAPLKEERLQARLLLQVH  540
           ********************************************  ********  ****

1XWL       DELILEAPKEEMERLCRLVPEVMEQAVTLRVPLKVDYHYGSTWYDAK  580      ⌐⌐ different points
BCRC11223  DELILEAPKEEMERLCRLVPEVMEQAVTLRVPLKVDYHYGSTWYDAK  587      └┘
Strain10   DELILEAPKEEMERLCRLVPEVMEQAVTLRVPLKVDYHYGSTWYDAK  587      ▓▓ delete residues
           ***********************************************
```

ISOLATED DNA POLYMERASES, KITS AND APPLICATIONS THEREOF

CROSS-REFERENCE TO RELATED APPLICATION

This application claims the priority benefits of U.S. provisional application Ser. No. 61/745,649, filed on Dec. 24, 2012. The entirety of the above-mentioned patent applications is hereby incorporated by reference herein and made a part of this specification.

BACKGROUND

1. Technical Field

The disclosure relates to isolated polymerases, kits and applications thereof.

2. Description of Related Art

Applications of thermostable enzymes are indisputably extensive, and the discovery of this type of enzymes has enabled the recent developments of several prominent biotechnologies, such as polymerase chain reaction (PCR). The polymerase chain reaction is a matured biotechnology capable of rapidly amplifying nucleic acid fragments in vitro so as to produce millions of amplification products of specific nucleic acid sequences. Currently, PCR has been broadly applied in various fields, including medicine, agriculture, biotechnology, forensic analysis, etc. The majority of PCR has adopted high temperature resistant thermostable DNA polymerases, and Taq DNA polymerase, for instance, is the most widely used DNA polymerases. Taq DNA polymerase, which is an enzyme found in thermophilic bacteria from the hot spring, has a high temperature resistance and is able to maintain a specific activity.

Following the development of the molecular diagnostic technologies, various types of polymerases of different functions have been found, such as Bst DNA polymerase. However, the resistance toward high temperatures for these enzymes still needs to be improved. Currently, it is essential to develop thermostable polymerase(s) to meet the needs of industry.

SUMMARY

The present disclosure provides an isolated deoxyribonucleic acid (DNA) polymerase comprising an amino acid sequence of SEQ ID NO. 1.

The present disclosure provides an isolated deoxyribonucleic acid (DNA) polymerase comprising an amino acid sequence of SEQ ID NO. 2.

The present disclosure provides a mutant of an isolated DNA polymerase, wherein the mutant has an amino acid sequence characterized in that at least one of five fragments: E309-A313, P348, V358-T365, A404-Q405 and P424-E445 is deleted from an amino acid sequences in a domain of 3'→5' exonuclease of the isolated DNA polymerase.

According to the embodiment of this disclosure, the mutant has a thermostability substantially equivalent to that of Bst DNA polymerase and a strand displacement activity substantially equivalent to that of the Bst DNA polymerase.

The present disclosure provides a kit including the isolated DNA polymerase(s), the mutant thereof or the combinations thereof.

According to the embodiment of this disclosure, the kit may be applicable for amplification reactions of nucleic acids, such as polymerase chain reactions (PCR), nucleic acid amplification, whole genome amplification (WGA), multiple displacement amplification (MDA) or DNA sequencing.

The kit including the isolated DNA polymerase(s), the mutant thereof or the combinations thereof as provided in the present disclosure has high thermostability and enzyme activity, thus improving the heat resistance levels, enhancing the storage stability and boosting potentials of applicability in various bio-medical fields.

In order to make the aforementioned and other objects, features and advantages of this disclosure comprehensible, embodiments accompanied with figures are described in detail below. It is to be understood that both the foregoing general description and the following detailed description are exemplary, and are intended to provide further explanation of this disclosure as claimed.

BRIEF DESCRIPTION OF THE DRAWINGS

The accompanying drawings are included to provide a further understanding of this disclosure, and are incorporated in and constitute a part of this specification. The drawings illustrate embodiments of this disclosure and, together with the description, serve to explain the principles of this disclosure.

FIG. 2A shows the amino acid sequences of Strain-10 and BCRC11223 according to one embodiment of this disclosure.

FIG. 2B shows the comparison of the amino acid sequences of Strain-10, BCRC11223 and Bst polymerase crystalline structure according to one embodiment of this disclosure.

FIG. 13 shows the deleted fragments of the amino acid sequences of Strain-10, BCRC11223 according to one embodiment of this disclosure.

DESCRIPTION OF EMBODIMENTS

Figure 1A:
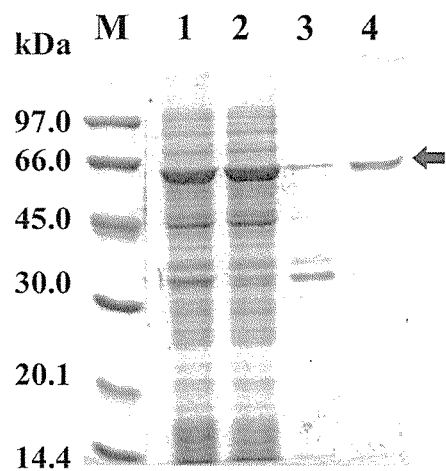
FIG. 1A shows the protein expression results of the transformant strain (pQE-11223) induced by IPTG and analyzed by column chromatography according to one embodiment of this disclosure.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

Herein, the DNA polymerase of interest is an unique polymerase called Bst DNA polymerase. The currently published *Geobacillus stearothermophilus* N3468 DNA polymerase I (abbreviated as polA) gene sequence (referring to GenBank accession number U33536) having a whole length of 2361 base pairs (bp) can encode the protein containing 876 amino acids. This enzyme obtained from high temperature resistant thermophile bacteria, *Bacillus stearothermophilus* (Bst), has fragments of 5'→3' exonuclease activity, 3'→5' exonuclease activity and 5'→3' polymerase activity. Currently, the commercialized product of Bst DNA polymerase is the large fragment of *Bacillus stearothermophilus* DNA polymerase protein without the fragment of exonuclease activity. The main feature of this enzyme is an active fragment capable of strand displacement. By using the large fragment of Bst DNA polymerase, a LAMP (loop-mediated isothermal amplification) reaction for the nucleic acids may be achieved. LAMP has several features: (1) Since it only requires thermostatic heating, the reaction may be completed by only using a thermostatic instrument, such as a water/dry bath or a heater; it is convenient, simple and practical for people in backlands. (2) Unlike the design of the general traditional PCR primer sets, it requires particularly designed primer sets, thus an overall specificity of the reaction may be enhanced. (3) The reaction time is more rapid as compared with other similar technologies, and thus is time saving. (4) High sensitivity, the sensitivity is about 100 to 1000 times of the general PCR. (5) In addition to using a conventional gel electrophoresis to test reaction end products of the LAMP, given that white precipitates are produced at the end of the reaction, a rather simple process of using a turbidimeter or a visual observation may also be adopted to determine whether the reaction is completed. (6) May be used in RNA samples. Unlike the traditional PCR, which requires to go through steps of heating and cooling repetitively, the features of the LAMP technology is to maintain the entire reaction at a constant temperature, and thus the production cost of the instrument may be lowered, the mechanical design becomes relatively simple, and the reaction time may also be greatly reduced. With the advantages mentioned above, the LAMP technology has received great attentions once it is introduced to the market. Hence, this enzyme, Bst DNA polymerase, involved in the LAMP reaction is of extra importance and uniqueness.

In order to make applications of Bst DNA polymerase more widely, and enable the high activity of Bst DNA polymerase to be maintained in different detections or storage transportations, this disclosure provides a simple and creative enzyme modification strategy to enhance the structural stability of the enzyme, so that a temperature tolerance of enzyme becomes higher, and the enzyme still maintains its special active state. Conceptual principles are summarized as below: in terms of temperature tolerance, Bst DNA polymerase is moderate thermophilic, and a suitable temperature thereof is 55~65° C. and it losses the activity at a temperature>70° C. On the other hand, Taq DNA polymerase is highly thermophilic, and a suitable temperature thereof is 7080° C. One common feature shared by these thermophilic polymerases of different sources lies in that these enzymes have structures similar to 3'→5' exonuclease but without the activity of 3'→5' exonuclease. Bst DNA polymerase, regardless in its dull-length or the large fragment thereof, also has the above-mentioned feature. The other DNA polymerases having the activity of 3'→5' exonuclease posses relatively low heat tolerance and are often inactivated when the ambient temperature is raised. Therefore, it is proposed by the Applicants that the thermophilic polymerase may become more thermostable when its structural portion having 3'→5' exonuclease is removed or deleted.

The temperature tolerance of Bst DNA polymerase is not as high as Taq DNA polymerase, and the storage of Bst DNA polymerase under the room temperature is not stable enough or long enough. The long-term storage and stability of reagents are prerequisites for in vitro diagnostic products, and enzymes are most likely to affect by the stability and storage conditions among the molecular diagnostic reagents. If the structures of the enzymes may be stabilized, the accuracy of the overall molecular diagnosis may be improved and stable expression may be achieved.

Gene Cloning of DNA Polymerase from *Geobacillus* sp.

Gene Cloning and Enzyme Purification of DNA Polymerase I

Gene Sequence Alignment of *Geobacillus* sp. polA

The currently published *Geobacillus stearothermophilus* N3468 DNA polymerase I (abbreviated as polA) gene sequence (referring to GenBank accession number U33536) having a whole length of 2361 base pairs (bp) can encode the protein containing 876 amino acids. The sequence of the enzyme has three domains, including the N-terminus $175^{th}$~$248^{th}$ amino acid residues as 5'→3 exonuclease domain, the middle $315^{th}$~$465^{th}$ amino acid residues as 3'→5' exonuclease domain and the C-terminus as the polymerase activity domain. In general, the commercialized product of Bst DNA polymerase I is the large fragment of the enzyme by removing the fragment of exonuclease domain. The "large" fragment spans from $289^{th}$ amino acid residue to the C-terminus ($289^{th}$~$876^{th}$ amino acids). In this experiment, through alignment with the amino acid sequence of the large fragment of DNA polymerase, the polA gene sequences of up to 99% similarity were identified in the genome database of the bacteria strains *G. stearothermophilus* strain 10 and *Geobacillus kaustophilus* BCRC11223. Afterward, primer design and gene cloning of the identified polA gene sequences were carried out so as to clone the polA gene(s) respectively from *G. stearothermophilus* strain 10 and *Geobacillus kaustophilus* BCRC11223 for gene expression.

Gene Cloning and Expression of *Geobacillus* Sp. polA

According to the alignment results, aiming at position $289^{th}$ amino acid of the polA gene(s) of *G. stearothermophilus* strain 10 and *G. kaustophilus* BCRC11223, DNA primers were designed (Bst-p B primer: 5'-GA GGATCC TCA GAA GAG GAA AAA CCG CT-3' (SEQ ID NO. 4); Bst-p K primer: 5'-GA GGTACC TTA TTT CGC ATC ATA CCA CG-3' (SEQ ID NO. 5)) for PCR reactions. After PCR reactions were carried out for amplification of the DNA fragments of the polA large fragment, the fragments inserted into the carrier pQE30 (Qiagen Co.) were transfected to *E. coli* host cells for expression. The expression vector pQE30 contains T5 promoter and the 6xHis tag. Isopropyl β-D-1-thiogalactopyranoside (IPTG) may be used to induce downstream gene expression of the promoter and $Ni^{2+}$-NTA agar column (Qiagen Co.) can be used to purify the copious expression of recombinant proteins. This experiment has successfully selected *E. coli* transformant strains respectively transfected with polA genes of *G. stearothermophilus* strain 10 and *G. kaustophilus* BCRC11223, and these transformant strains were named as *E. coli* (pQE-g10polA) and *E. coli* (pQE-11223polA). The sequences of the cloned genes were confirmed by DNA sequencing as the correct sequences. The cloned large fragment of DNA polymerase starts from $289^{th}$ amino acid residue Ala with a total length of 580 amino acids, and the N-terminus of the sequence is connected and expressed with the 6xHis tag for facilitating the subsequent protein purification.

Figure 1B:
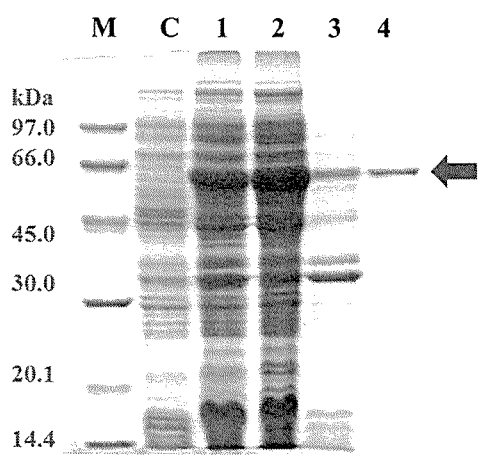
FIG. 1B shows the protein expression results of the transformant strain (pQE-g10) induced by IPTG and analyzed by column chromatography according to one embodiment of this disclosure.

The selected transformant strains of *E. coli* were induced by IPTG to induce T5 promoter of the plasmid for gene expression, and then the bacteria were harvested. The bacteria were washed and redissolved with 20 ml of 50 mM Tris-HCl, pH 8.0, followed by breaking the bacteria using ultrasonic cell disrupter (Ultrasonic processor UP-800, ChromTech, MN, USA), and SDS-PAGE column chromatography was used to evaluate gene expression. FIG. 1A shows the protein expression results of the transformant strain (pQE-11223) induced by IPTG and analyzed by column chromatography according to one embodiment of this disclosure. FIG. 1B shows the protein expression results of the transformant strain (pQE-g10) induced by IPTG and analyzed by column chromatography according to one embodiment of this disclosure. In the figures, the column M: protein markers; column C: *E. coli* pQE30 as the control group; column 1: cell extract; column 2: supernatant; column 3: cell debris; column 4: purified enzymes. The results showed that *E. coli* transformant strains indeed can express a lot of the cloned polA gene, and the expressed soluble polA proteins account for about 80~90% of all the expressed polA proteins (columns 1 & 2) with only a small amount of insoluble polA proteins produced (column 3). After purified by $Ni^{2+}$-NTA agar column, the large fragment of DNA polymerase I in high purity was obtained, and the molecular weight of the enzyme is as expected of a size about 65 kDa (column 4 in the figure). The cloned and purified enzymes from *G. stearothermophilus* Strain 10 and *G. kaustophilus* BCRC11223 were named as Bst g10 DNA polymerase and Bku DNA polymerase I respectively, and their amino acid sequences are listed as Strain10 (SEQ ID NO. 1) and BCRC11223 (SEQ ID NO. 2).

The present disclosure provides an isolated DNA polymerase, i.e. Bst g10 DNA polymerase with the amino acid sequence including SEQ ID NO. 1. Also the present disclosure provides an isolated DNA polymerase, i.e. Bku DNA polymerase with the amino acid sequence including SEQ ID NO. 2.

This disclosure identifies the different structural points between Bst DNA polymerase and Taq DNA polymerase by comparing the structures of both. Then, the key structural position(s) involved in the thermostability are analyzed and identified through the technical assistances of bioinformatics and molecular dynamics simulations. Next, Bst DNA polymerase is modified by using the genetic engineering and protein engineering techniques to enhance its thermostability and enzyme activity. It is intended that not only the heat tolerability of Bst DNA polymerase may be enhanced, but also the storage stability of Bst DNA polymerase may also be improved. Hence, potential applications of Bst DNA polymerase in a variety of biomedical testing fields would be promoted.

The sequences and structures of Bst DNA polymerase and Taq DNA polymerase can be compared using the technical assistances of bioinformatics and molecular dynamics simulations. It is speculated that deletion of the structural portion(s) having 3'→5' exonuclease activity of the thermophilic polymerase can make the overall structure become more thermostable. The fragment of 3'→5' exonuclease activity of Bst DNA polymerase has nearly 40 amino acids more than that of Taq DNA polymerase. Therefore, it is speculated that, through the deletion of these additional amino acids, the resultant enzyme structure would have a configuration similar to that of Taq DNA polymerase. That is, the resultant (modified) enzyme may have enhanced thermostability and keep the specific activity of Bst DNA polymerase. In the Klenow fragment (KF) being most intolerant to high temperatures, as compared to the other two enzyme structures, there are even more additional amino acids. This disclosure has great breakthroughs when compared to the conventional methods of adopting random point mutations or the time-consuming screening of large amounts of mutants.

This disclosure relates to a method for enhancing a thermostability of polymerase, and the method may be summarized to include at least the following two processes:

Process (A): comparing a reference thermostable polymerase and a target polymerase and identifying excess amino acids in the target thermostable polymerase. For example, the reference thermostable polymerase is Taq DNA polymerase, while the target polymerase is Bst DNA polymerase. The amino acid sequence in the structural portion (or domain) of 3'→5' exonuclease of the target thermostable polymerase is compared with the amino acid sequence in the structural portion (or domain) of 3'→5 exonuclease of the reference thermostable polymerase to identify the excess amino acids in the amino acid sequence in the structural portion (or domain) of 3'→5' exonuclease of the target thermostable polymerase. For example, the amino acid sequences in the structural portion (or domain) of 3'→5' exonuclease of the target thermostable polymerase is compared with the amino acid sequence in the structural portion (or domain) of 3'→5' exonuclease of the reference thermostable polymerase by using multiple sequence alignment. The excess amino acids in the amino acid sequence in the structural portion (or domain) of 3'→5' exonuclease of the target thermostable polymerase are identified using bioinformatics technologies, such as molecular docking, molecular dynamics simulation and the like.

Process (B): using genetic engineering and protein engineering techniques to delete the identified excess amino acids in the target thermostable polymerase so as to obtain at least a mutant of the target thermostable polymerase through cloning, expression and purification technologies.

Further details of the above-mentioned processes and technologies will be described in the following contexts.

Bioinformatics and molecular dynamics simulation analysis of Bst DNA polymerase.

The large fragment crystalline structure (PDB id: 1XWL) of the Bst DNA polymerase I is used as a template (a sequence length of approximately 580 amino acids). A Sybyl-X is subsequently used to apply an AMBER7 F99 charge force field to the proteins, then the protein fragments (38 amino acids) are removed, and an energy minimization (using a configuration energy gap between $n^{th}$ and $n^{-1th}$ being less than 0.025 kcal/(mol*A) or a maximum number of operations being 50000 steps as an termination point) is performed to adjust collisions between the amino acids. A docking analysis of macromolecules is conducted to the processed protein structures (i.e. the target protein) through ParaDock and HADDOCK (High Ambiguity Driven protein-protein Docking). ParaDock may construct any sequence of DNA structure and enable a flexible DNA structure to dock to the target protein. HADDOCK may perform a method of flexible docking of the DNA to the target protein while specifying possible active residues of the DNA and the target protein referring to the large fragment crystalline structure (PDB id: 1XWL) of the Bst DNA polymerase I. Eventually, a stability of the complex structure of DNA and protein generated from the docking result is confirmed via a molecular dynamics simulation with Discovery Studio 2.0. In detail, a CHARMm force field is firstly applied to the complex structure, a water molecule environmental simulation covering a complex binding region is constructed, and two-stages of energy minimization (steepest descent and conjugate gradient) are then being entered so as to optimize the complex structure; next, three stages comprised of heating, equilibration and production are performed, wherein a starting temperature of 50K is gradually raised to 300K during the process of heating, energy of the complex structure is moderately distributed so as to maintain a thermal equilibrium during the process of equilibration, and an appropriate thermodynamic ensemble (e.g., an isothermal-isobaric ensemble; NPT) is selected for sampling during the process of production; finally, a trajectory analysis procedure is adopted to analyze the total energy of the complex structure and the structural root-mean-square deviation (RMSD) following the change of time, and if the RMSD value is less than 2 Å, it indicates that the simulation result is favorable and a subsequent analysis may be performed.

TABLE 1

| TOOL | APPLICATION |
| --- | --- |
| Swiss-Pdb Viewer 3.7 (software) | homology modeling |
| Sybyl-X (software) | delete mutation |
| ParaDock (web server) | docking |
| HADDOCK (web server) | docking |
| Discovery Studio 2.0 (software) | molecular dynamics simulation |
| PyMOL v0.99 (software) | Viewer |

As mentioned above, the cloned and purified enzymes from *G. stearothermophilus* Strain 10 and *G. kaustophilus* BCRC11223 were named as Bst g10 DNA polymerase and Bleu DNA polymerase respectively, and their amino acid sequences are listed as Strain10 (SEQ ID NO. 1) and BCRC11223 (SEQ ID NO. 2). Both sequences of Strain-10 and BCRC11223 have a total sequence length of 878 amino acids. The amino acid sequences of Strain-10 and BCRC11223 in FIG. 2A marked by gray blocks refer to the large fragments of DNA polymerase I. Herein, only the portions of the large fragment of Bst DNA polymerase (a sequence length of 587 amino acids) are considered for both sequences, in reference to the crystalline structure of the large fragment of Bst DNA polymerase (PDB id: 1XWL; a sequence length of 580 amino acids), the multiple sequence alignment using ClustalW2 [online], EMBL-EBI 2013, retrieved from the Internet: (URL: world wide web: ebi.ac.uk/Tools/msa/clustalw2/) is performed. Then, it is learned that a sequence similarity between the Strain-10, the BCRC11223 and the Bst enzyme crystalline structure is as high as 99%. From FIG. 2B, by comparing the amino acid sequences of Strain-10, BCRC11223 with Bst enzyme crystalline structure, the dotted blocks marked on the sequences refer to different points (amino acid residues) among these sequences and the gray blocks refer to the amino acid(s) to be deleted (deleted residues) according to this disclosure. BCRC11223 is the amino acid sequence of the DNA polymerase of *G. kaustophilus* BCRC11223; Strain10 is the amino acid sequence of the DNA polymerase of *G. stearothermophilus* Strain 10; and 1XWL is the amino acid sequence of the DNA polymerase of *G. stearothermophilus* N3468. Herein, five gray blocks, E309-A313, P348, V358-T365, A404-Q405 and P424-E445, are marked to represent five fragments that are considered to be deleted, i.e. deleted residues. In later stages, deletion of one or more of these five fragments is simulated to evaluate the stability and the practicability of the modified enzyme structure(s) is verified based on the calculation results of molecular docking and molecular dynamics simulation.

Figure 3:
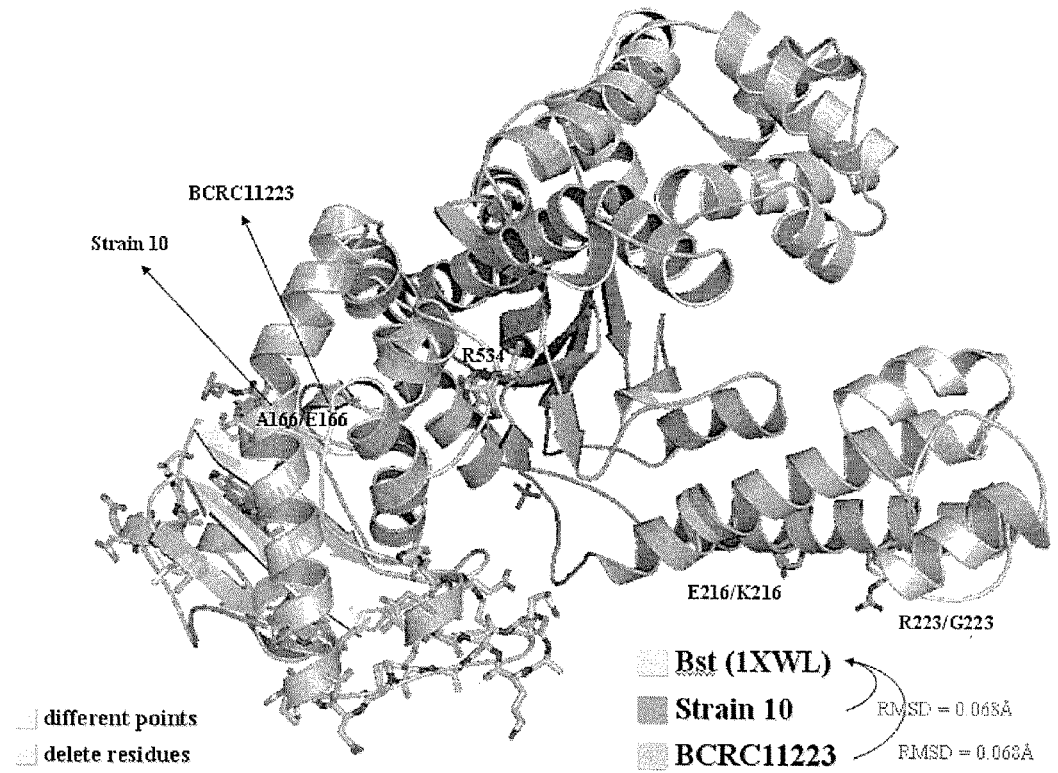
FIG. 3 shows a homology modeling result of Strain-10 and BCRC11223 according to one embodiment of this disclosure.

Subsequently, a homology modeling analysis is performed using Swiss-Model [online], Swiss Institute of Bioinformatics, 2009, retrieved from the Internet: (URL: swissmodel.expasy.org/), and through using the Bst enzyme crystalline structure as the template to obtain the simulation structures of the two replication sequences (the sequence length of 580 amino acids), and then through superimposing the simulation structures to the original Bst enzyme crystalline structure, the resulting RMSD value is 0.068 Å, which indicates that the simulation structures and the crystalline structure are very similar. FIG. 3 shows a homology modeling result of Strain-10 and BCRC11223. In FIG. 3, the color gray represents Bst crystalline structure, while the color purple represents Strain-10 and the color cyan represents BCRC11223; the color yellow refers to different points of sequences, while the color pink refers to the amino acids to be deleted (deleted residues).

Based on the previous comparison results of Bst polymerase and Taq polymerase (PDB id: 1KTQ; a sequence length of 535 amino acids), these 38 amino acids (E309, E310, M311, L312, A313, P348, V358, A359, W360, L361, G362, D363, E364, T365, A404, Q405, P424, D425, E426, A427, V428, Y429, G430, K431, G432, A433, K434, R435, A436, V437, P438, D439, E440, P441, V442, L443, A444, E445) of Bst DNA polymerase are excess amino acids when compared to Taq polymerase. It is assumed that if some or all of these excess 38 amino acids are deleted from the amino acid sequence(s), then a sequence length of the amino acid sequence(s) after the deletion becomes 542 amino acids, the temperature tolerance of the Bst polymerase is expected to be improved. These 38 residues are conserved sequences of the Bst enzyme crystalline structure, Strain-10 and BCRC11223. Simulated deletion mutation is performed using Sybyl-X, the simulation structure is loaded and the simulation steps of water removal, hydrogenation, adding charges, deleting amino acid residues (monomers), and energy minimization are sequentially performed.

Finally, the simulation structures of Strain-10 and BCRC11223, which have deleted these 38 residues and went through the energy minimization processes, are superimposed to the Bst enzyme crystalline structure (without deleting these 38 residues) and the Taq enzyme crystalline structure, and the RMSD values of Strain-10—Bst, BCRC11223—Bst, Strain-10—Taq, and BCRC11223—Taq are respectively 0.8930 Å, 1.0817 Å, 3.2009 Å and 3.1912 Å. The results indicate that, from a structural point of view, the simulation structures of the two replication sequences are similar to the Bst enzyme crystalline structure but different from the Taq enzyme crystalline structure.

Nucleic Acid (DNA) and Protein Docking Analysis

ParaDock [online], retrieved from the Internet: (URL: bioinfo3d.cs.tau.ac.il/ParaDock/index.html) is an ab initio molecular docking algorithm of flexible nucleic acid docking to a rigid protein. Herein, ParaDock totally relies on the protein structure to estimate its complex with the B-form nucleic acid, and uses the nucleic acid and a protein binding property (an electrostatic and an amino acids tendency) to detect a complementarity of a local rigid shape. The repetition of the B-form nucleic acid structure is being used to construct curved elongated nucleic acid molecules, and then processes of scoring and sorting are performed via geometric complementary. When using ParaDock to perform the molecular docking, it only requires inputting the protein structure (pdb format) to produce a plurality of protein and nucleic acid molecule complexes (docking conformations), and the process includes four main stages:

(1) Local rigid docking results of the proteins and short segments of nucleic acid are produced and screened through ParaDock.

(2) The dockings of co-linear pairs and co-planar triplets are found.

As a result, plane conic (second-order polynomial) curves in coordination with the docking results are then produced.

(3) Molecular docking results are constructed along candidate curves.

(4) The scoring and the sorting of the docking results are performed via geometric complementary.

Since the ParaDock does not perform a treatment to the flexibility of the proteins, the protein structures before and after the docking are the same. Moreover, a user needs to define a conformation of the proteins in a bounded state or an unbounded state and set a number for the expected docking results to be received, and the final results are sent to a mailbox chosen by the user.

HADDOCK (High Ambiguity Driven protein-protein Docking) [online], NMR Department, 2008, retrieved from the Internet: (URL: haddock.science.uu.nl/services/HADDOCK/haddock.php) is a molecular docking method driven by experimental knowledge. The experimental knowledge relates to information in form of molecular compositions or surface regions in relative orientations thereof; and the information may be derived from mutagenesis, mass spectrometry or nuclear magnetic resonance (NMR) experiments (chemical shift perturbation, residual dual magnetic moment or hydrogen-deuterium exchange, classical NMR distance limit). When the experimental information is scarce or lacking, a bioinformatics prediction may be used as an interface; HADDOCK version 2.0 supports nucleic acid and small molecule, may handle a wide range of experimental data, and provides a improved molecular docking program; HADDOCK has been applied to a variety of problems, including complexes of protein and protein, protein and nucleic acid, protein and oligosaccharide, protein and small molecule, and so forth. Unlike many other molecular docking programs, HADDOCK allows the molecules on a side chain or a backbone to have conformational changes during the process of complex formation; and may directly support the molecular dockings of NMR and other protein database structures. A HADDOCK server entrance provides three types of web interfaces: Easy, Expert and Guru. The experimental data of the molecules are tabulated into active residues and passive residues, wherein the active residues are residues within the complex that directly involved in an interaction, and the passive residues are residues that surrounding the surface of the protein and possibly involved in the interaction. Herein, the molecular docking is performed using the easy interface, the user only have to load an initial structure and list the residues that involved in the interaction. Since HADDOCK, unlike ParaDock, does not provide the molecular docking for an arbitrary sequence of B-form nucleic acid, the nucleic acids (approximately 11 residues), which have derived from the crystalline structure (PDB id: 4BDP) of the Bst and nucleic acid complexes, are taken as docking subjects. The energy minimized Strain-10 or BCRC11223 simulation structures are loaded in a first molecule list of the interface, residue numbers in act (267, 269, 289, 293, 323, 326, 328, 331, 333, 339, 340, 418, 482, 500, 508, and 541) are entered into the column fields of the active residues, and at the same time, the type of the docking molecule is confirmed to be selected as protein (default). The nucleic acid structures are subsequently loaded into a second molecule list, residue numbers in act (3, 4, 5, 6, 7, 8, 25, 26, 27, 28, and 29) are also entered into the column fields of the active residues, and then the type of the docking molecule is confirmed to be selected as nucleic acid (DNA). If the passive residues are not particularly specified, then an auto-define may be checked (the program automatically assigns the passive residues to be the residues surrounding the active residues) to complete the setting. Finally, an email address and a password are inputted, and then the program schedules the task into a team of waiting to be executed, wherein the results thereof are listed into the top 10 groups according to the scores, and each group only shows the 4 best docking conformations.

Molecular Dynamics Simulation Analysis of DNA-Enzyme Complex

Molecular dynamics simulation operations in Discovery Studio 2.0 are divided into the following steps: system preparation, twice energy minimization, heating, equilibration, production, and trajectory analysis.

Figure 4:
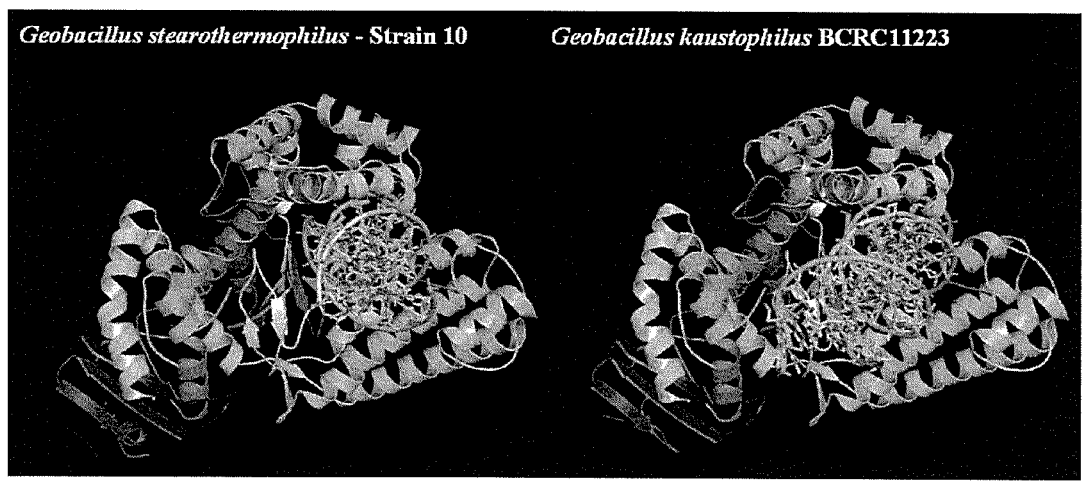
FIG. 4 shows ParaDock molecular docking results of Strain-10 and BCRC11223 according to one embodiment of this disclosure.

The similarity between the two replication sequences of Strain-10 and BCRC11223 simulation structures and the Bst enzyme crystalline structure at the large fragment is as high as 99%. Although some of the amino acids are different, the simulation structures of the two replication sequences are still very similar to the Bst enzyme crystalline structure (the RMSD value is less than 1 Å). Taq polymerase commonly used in the experiments can withstand a high temperature (70 to 80° C.)., and a suitable temperature for the Bst polymerase is between 55 to 65° C. (temperature>70° C., loss of activity). By comparing these two enzymes, it is learned that the Bst polymerase has 38 amino acids more than the Taq polymerase. The computer simulation method is used to explore that whether the Bst polymerase may still form a stable complex with the nucleic acid (DNA) if the excess amino acids of the Bst enzyme structure are removed. Herein, two docking programs, ParaDock and HADDOCK, applicable for the macromolecules are used to perform the structural simulation and the molecular docking of the nucleic acid. ParaDock, according to the protein structure provided, searches for a possible complementary area under the provision of not changing the conformation (rigid structure), docks the inbuilt B-form nucleic acid to the complementary area, and finally outputs 10 molecular docking results. Moreover, referring to the crystalline structure of the known Bst-nucleic acid complex, the docking results (FIG. 4) for the subsequent analysis are selected according to a conformation direction of the nucleic acid thereof. In FIG. 4, the left figure shows ParaDock results of Strain-10 and the right figure shows ParaDock results of BCRC11223.

Figure 5:
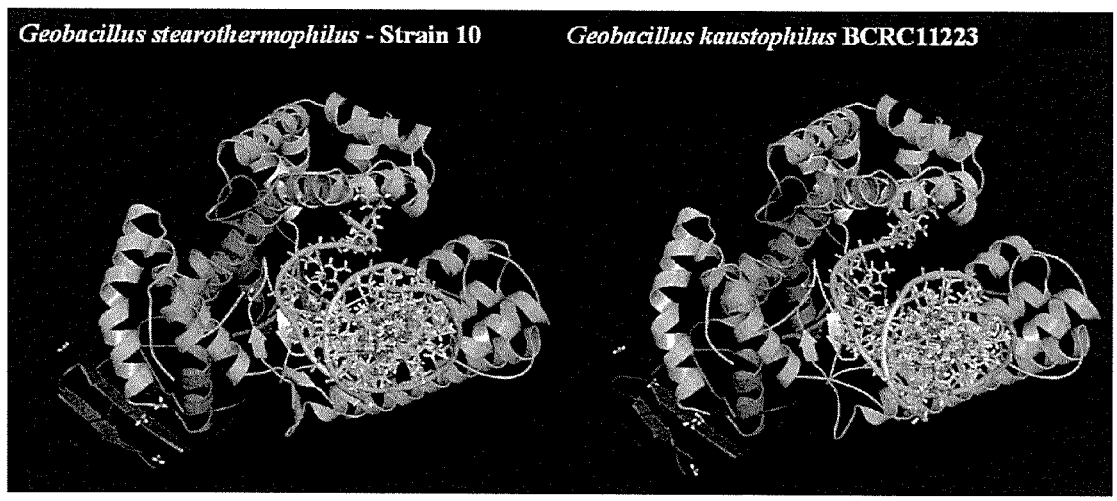
FIG. 5 shows HADDOCK molecular docking results of Strain-10 and BCRC11223 according to one embodiment of this disclosure.
Figure 6:
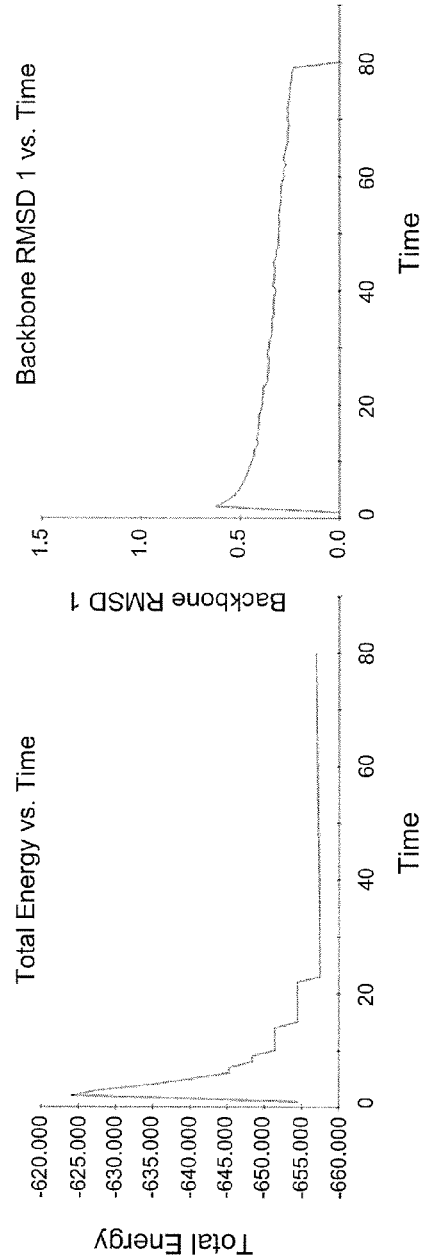
FIG. 6 shows a ParaDock dynamic simulation result of Strain-10 according to one embodiment of this disclosure.
Figure 7:
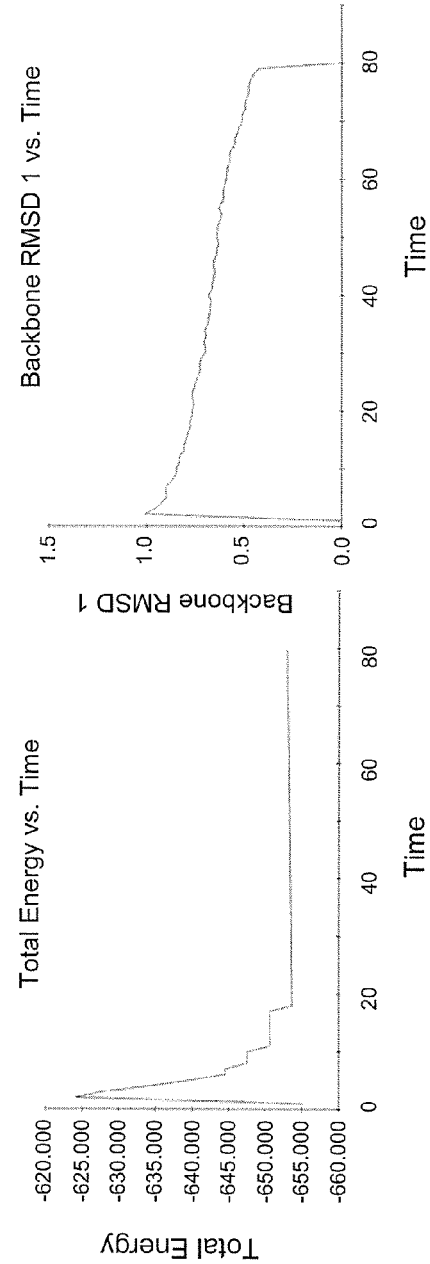
FIG. 7 shows a HADDOCK dynamic simulation result of Strain-10 according to one embodiment of this disclosure.
Figure 8:
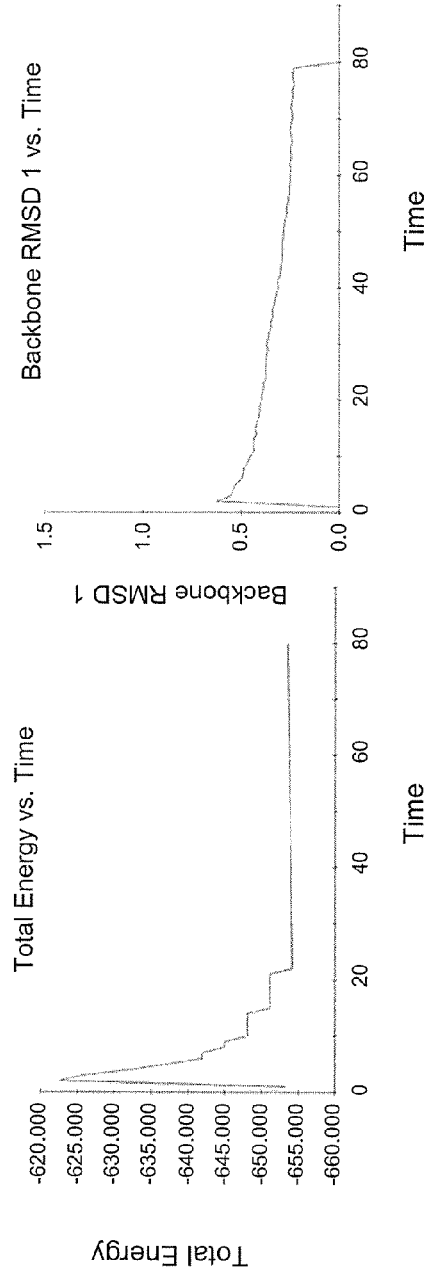
FIG. 8 shows a ParaDock dynamic simulation result of BCRC11223 according to one embodiment of this disclosure.
Figure 9:
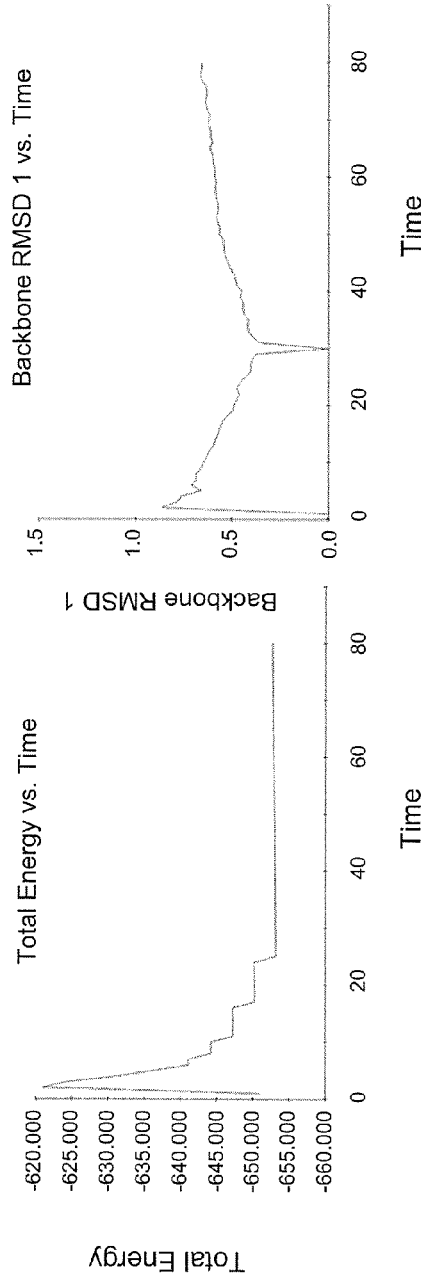
FIG. 9 shows a HADDOCK dynamic simulation result (I) of BCRC11223 according to one embodiment of this disclosure.
Figure 10:
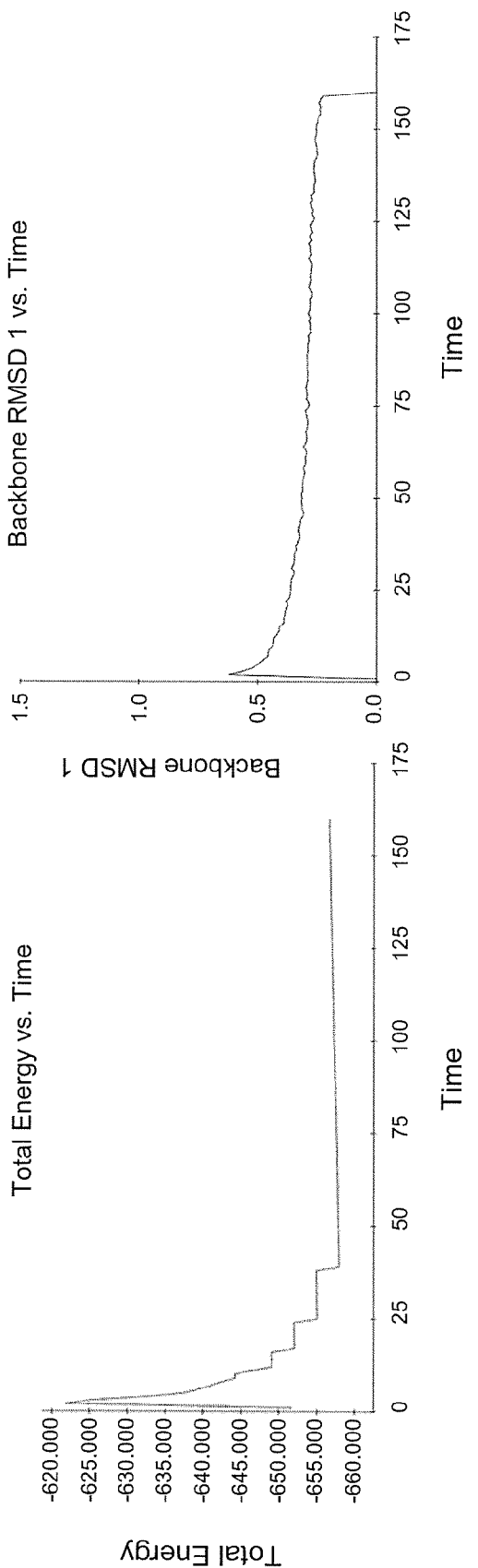
FIG. 10 shows a HADDOCK dynamic simulation result (II) of BCRC11223 according to one embodiment of this disclosure.

HADDOCK, through defining the active residues of the protein and nucleic acid interaction, performs the flexible molecular docking by taken both structures of protein and nucleic acid structures as elastomers. Since no inbuilt nucleic acid structure is available for use, the nucleic acid structure of the Bst-nucleic acid complex is used to dock to the simulation structures; and similarly, the docking results (FIG. 5) for the subsequent analysis are selected according to the conformation of the nucleic acid in the crystalline structure. In FIG. 5, the left figure shows HADDOCK results of Strain-10 complex and the right figure shows HADDOCK results of BCRC11223 complex. Molecular dockings are performed by using ParaDock and HADDOCK respectively to both of Strain-10 and BCRC11223 simulation structures (in total four docking results). Next, the molecular dynamics simulation is performed to examine the stability of the complex, through dynamic analysis tools provided by the Discovery studio 2.0, by adding water molecules to simulate the real situation and performing twice energy minimization, and via the heating step to raise the temperature from 50K to 300K, an enhancement of the complex energy is able to cross an energy barrier and go from a local energy minimization to a completely energy minimization. Finally, the steps of equilibration and production are performed by maintaining the temperature at 300K, observing the change of the complex conformation along with time, patterning the aforementioned results via a trajectory analysis, respectively analyzing the changes in total energy versus time and RMSD, and obtaining the analysis result of Strain-10 complex (i.e. the docking result of the nucleic acid structure and Strain-10 simulation structure from ParaDock) (FIG. 6), the analysis result of Strain-10 complex (i.e. the docking result of the nucleic acid structure and Strain-10 simulation structure from HADDOCK) (FIG. 7), the analysis result of BCRC11223 complex (i.e. the docking result of the nucleic acid structure and BCRC11223 simulation structure from ParaDock) (FIG. 8), the analysis result of BCRC11223 complex (i.e. the docking result of the nucleic acid structure and BCRC11223 simulation structure from HADDOCK) (FIG. 9). The favorable results are that the complex may stably exist as the total energy of the complex approaches a constant value over the time and the RMSD value of the complex becomes decreased over the time. In the HADDOCK dynamic simulation results of BCRC11223 complex, there is a sudden drop at 30 femtoseconds ($10^{-15}$ s) when comparing the RMSD, and therefore, the simulation time for the examination is doubled. As a result, the total energy becomes stable and the RMSD value gradually decreases (FIG. 10). It is speculated that the sudden drop in RMSD may be caused by a human operator error, because each step in the simulation steps is independent of the others.

Establishing of the Comparison Method for Enzyme Activity Tests

Fluorescent DNA Polymerase Activity Assay

Fluorescence is good for being sensitive, simple, stable and well-developed. This disclosure applies the fluorescent product for the detection of DNA polymerase activity to establish fluorescence measuring approach of enzyme activity. Because PicoGreen fluorescent dye has better sensitivity and high specificity for double-stranded DNA (dsDNA), the experimental analysis is not affected by pollutants and no further purification is required to obtain precise and accurate quantitative results of dsDNA. In this study, after assessment, PicoGreen fluorescent dye is chosen as the experimental fluorescent dye, worked with NanoDrop3300 fluorospectrometer (Thermo Fisher Scientific, Wilmington, Del., USA), for the quantitative analysis of dsDNA concentration.

Determination of dsDNA Quantitation Standardized Curve

Figure 11:
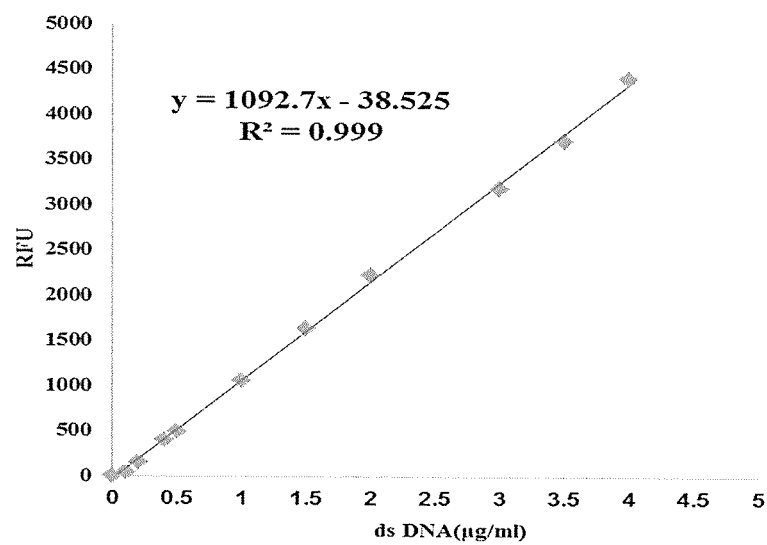
FIG. 11 shows the quantitation standardized curve for single stranded DNA using the dye PicoGreen according to one embodiment of this disclosure.

The quantitation standardized curve of dsDNA concentration is determined by using Quant-iT™ PicoGreen® dsDNA Assay Kit (purchased from Invitrogen) and M13mp18 dsDNA (purchased from New England Biolabs). First, 20 µg/ml M13mp18 dsDNA solution is prepared, and followed by adding 0, 0.2, 0.4, 0.8, 1, 2, 3, 4, 5, 6, 7, 8 and 9 µl of the solution into the brown microcentrifuge tube, adding 1×TE buffer (10 mM Tris-HCl buffer pH 7.9, 1 mM EDTA) to 20 µl, then adding 20 µl of 200-fold diluted PicoGreen dye, and mixed at the room temperature for 5 minutes. NanoDrop 3300 fluorospectrometer is set at the excitation wavelength of 470 nm (Blue LED) and emission wavelength of 525 nm for detection and a linear regression curve of the dsDNA concentrations and values of relative fluorescence units (RFU values) is obtained. The linear detection range spans over 0~4 µg/ml of dsDNA concentrations, $R^2$ value is 0.9999, the linear equation Y=1092.7X−38.525, wherein Y is the RFU value; X is the dsDNA concentration (see FIG. 11), which is used as the criteria for conversion for subsequent quantitation of dsDNA. FIG. 11 shows the quantitation standardized curve for single stranded DNA using the dye PicoGreen according to one embodiment of this disclosure.

Setting of DNA Polymerase Activity Assay

Setting of DNA polymerase activity assay is modified based on the method proposed by Heidi Tveit and Tom Kristensen in 2001. Before the enzyme reaction, single-stranded DNA (ssDNA) linked with the primer, i.e. annealing primer-template mixture, is firstly prepared. The primer annealing process was carried out by taking 28 µg (14 pmol) M13mp18 ssDNA (purchased from New England Biolabs), adding 1 pmol of UP primer (SEQ ID NO. 6: 5'-TTCCCAGTCAC-GACGTTGTAAAACGACGGCCAGTG-3') designed and synthesized for the M13mp18 DNA sequence, 10× reaction buffer (200 mM Tris-HCl buffer pH8.8, 100 mM $(NH_4)_2SO_4$, 100 mM KCl, 20 mM $MgSO_4$, 1.0% Triton X-100) and 1×TE buffer (or deionized water) to a total volume of 100 being mixed evenly and placed under 70° C. for reaction for 5 mM, cooling slowly to the room temperature and stored at −20° C. The total volume for the enzyme reaction was 20 µl, the reaction mixture including: 2.4 µl of the two-fold diluted annealing primer-template mixture, 10 mM dNTP 2 µl, 10× reaction buffer 2 deionized water 9.6 µl, 2 µl of Bst polymerase I (finally 0.05 U or 16 µg/ml). After reacted at 65° C. for 30 min, 0.8 µl of 0.5M EDTA was added to terminate the reaction. Then, after adding an equal volume of PicoGreen fluorescence dye for reaction at room temperature for 5 minutes, analysis was performed.

Figure 12:
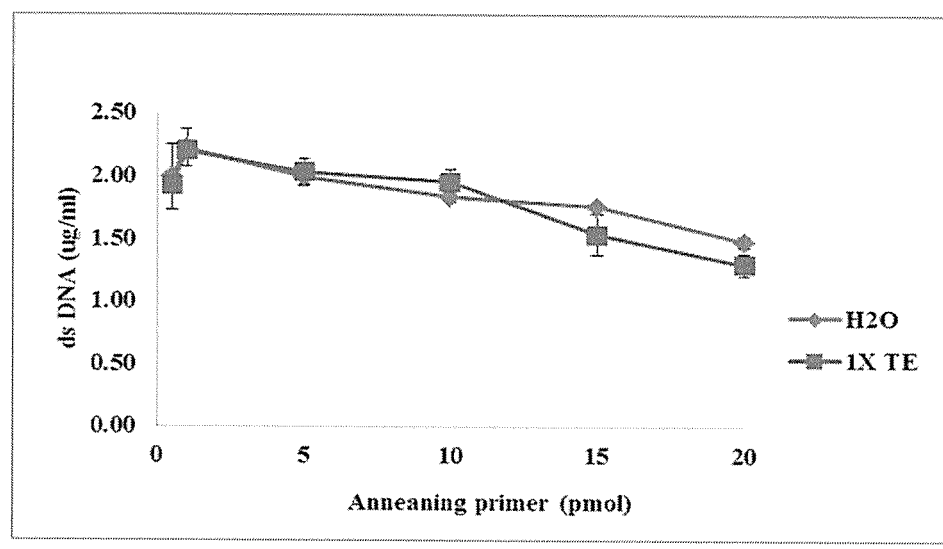
FIG. 12 shows the association of the primer concentrations in the annealing primer-template mixtures versus the dsDNA product concentrations resultant from the enzyme(s).
Figure 14A:
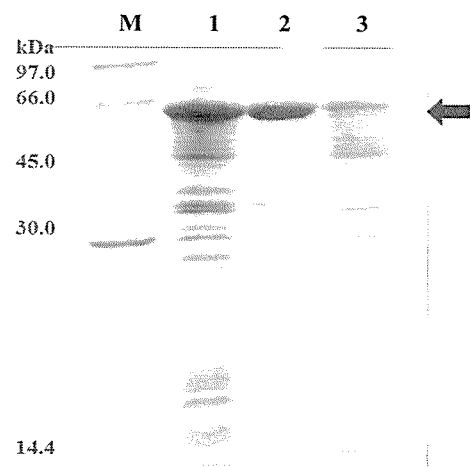
FIG. 14A shows the purification results of the enzyme expressed by BCRC11223 transformed strain *E. coli* (pQE-123 del 1).
Figure 14B:
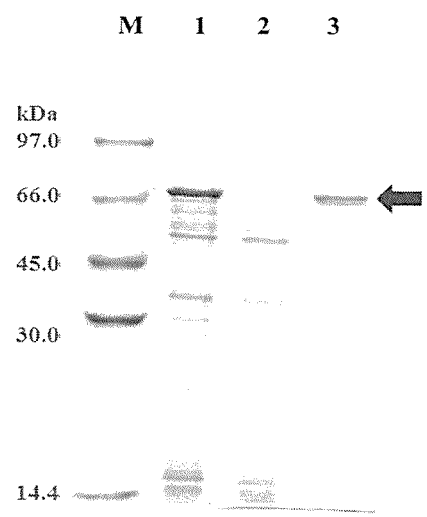
FIG. 14B shows the purification results of the enzyme expressed by BCRC11223 transformed strain *E. coli* (pQE-123 del 3).
Figure 15A:
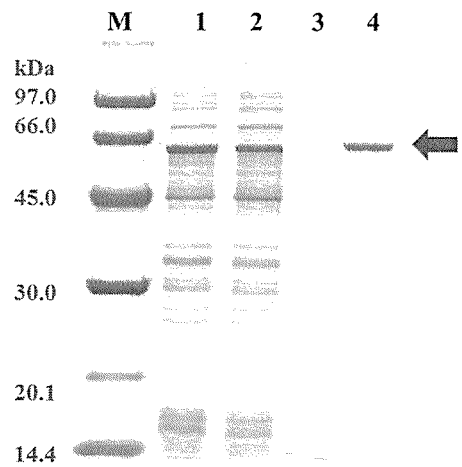
FIG. 15A shows the purification results of the enzyme expressed by BCRC11223 transformed strain *E. coli* (pQE-123 del 4).
Figure 15B:
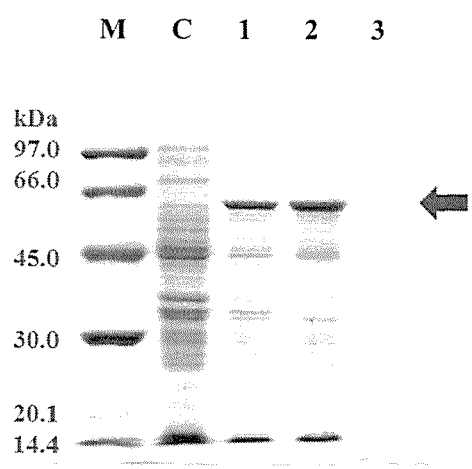
FIG. 15B shows the purification results of the enzyme expressed by BCRC11223 transformed strain *E. coli* (pQE-123 del 1B).
Figure 15C:
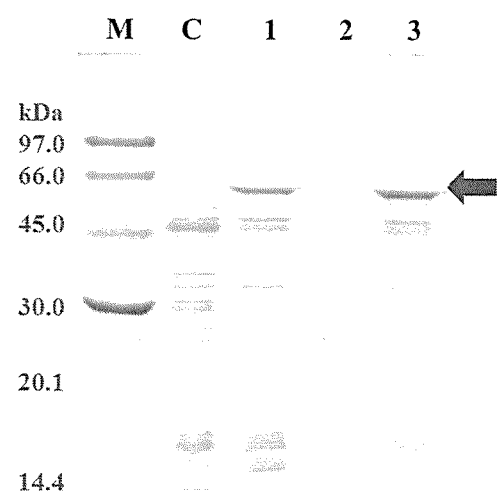
FIG. 15C shows the purification results of the enzyme expressed by BCRC11223 transformed strain *E. coli* (pQE-123 del all).

According to previous conditions in the literature, the concentration of the annealing primer-template mixture is 24 pmol. But during the activity tests, it is found that higher concentrations of primers lead to lowers concentrations of dsDNA. To find the optimal conditions for the enzyme reaction, it is designed to exploit different primer concentrations (0.5~20 pmol) for the enzyme activity assays. The results are shown in FIG. 2, when the primer concentrations ranging between 0.5~1 pmol, the activity of Bst DNA polymerase reaches the maximum (dsDNA concentration reaching 2.23

μg/ml), and when the primer concentration is higher than 1 pmol, the concentration of the product dsDNA begins to fall. When the primer concentration reaches 20 pmol, the product concentration is only 1.33 If compared with the condition of 1 pmol primer concentration, the concentration of the generated dsDNA differs by 0.9 μg/ml. If taking the amount of the generated dsDNA under the condition of 1 pmol primer concentration as 100% of the relative enzyme activity, the relative enzyme activity under the condition of 20 pmol primer concentration keeps only 59.6% of the original activity. Further results also indicate that using TE buffer or deionized water to prepare annealing primer-template mixture has no significant effects on enzyme conversion activity. Based on the results, the optimal concentration of primers of the annealing primer-template mixture for the reaction was set to be 1 pmol, as reaction conditions for the subsequent Bst DNA polymerase activity assays. FIG. 12 shows the association of the primer concentrations in the annealing primer-template mixtures versus the dsDNA product concentrations resultant from the enzyme(s).

DNA Polymerase Activity Assay of *Geobacillus* Sp.

DNA Polymerase Activity Assay

The purified enzyme was diluted and stored in the storage buffer (10 mM Tris-HCl pH7.9, 50 mM KCl, 1 mM DTT, 0.1 mM EDTA, 0.1% Triton X-100, 50% glycerol) at −20° C. The enzyme activity assays were as described previously and the enzyme amount of the commercial available Bst DNA polymerase I (Lucigen Co.) was set to be 0.05 U (16 μg/ml). The amount of the enzyme protein of the cloned and purified Bst g10 DNA polymerase I and Bku DNA polymerase was set to be 16 μg/ml for the activity assay. The total volume of the enzyme reaction was 20 μl. After adding the enzyme, the mixture was reacted at 65° C. for 30 min, 0.8 μl of 0.5M EDTA was added to terminate the reaction. Then, after adding an equal volume of PicoGreen fluorescence dye for reaction at room temperature for 5 minutes, activity analysis was performed. The results are shown in Table 1, 0.05 U of the commercial available Bst DNA polymerase I (Lucigen Co.) can generate 1.56±0.03 μg/ml dsDNA under the reaction conditions of this experiment. However, at the same protein concentration (16 μg/ml), Bst g10 DNA polymerase I can generate 1.68±0.07 μg/ml dsDNA; Bku DNA polymerase I can generate 1.80±0.04 μg/ml dsDNA. From these results, it is shown that the cloned DNA polymerase(s) of this experiment has better activity than the commercial available Bst DNA polymerase I (Lucigen Co.), at the same protein concentration.

TABLE 2

| Enzyme (0.05 U or 16 μg/ml) | Generated dsDNA (μg/ml) |
|---|---|
| Commercially available Bst DNA polymerase I (Lucigen Co.) | 1.56 ± 0.03 |
| Bst g10 DNA polymerase I | 1.68 ± 0.07 |
| Bku DNA polymerase I | 1.80 ± 0.04 |

Figure 13:
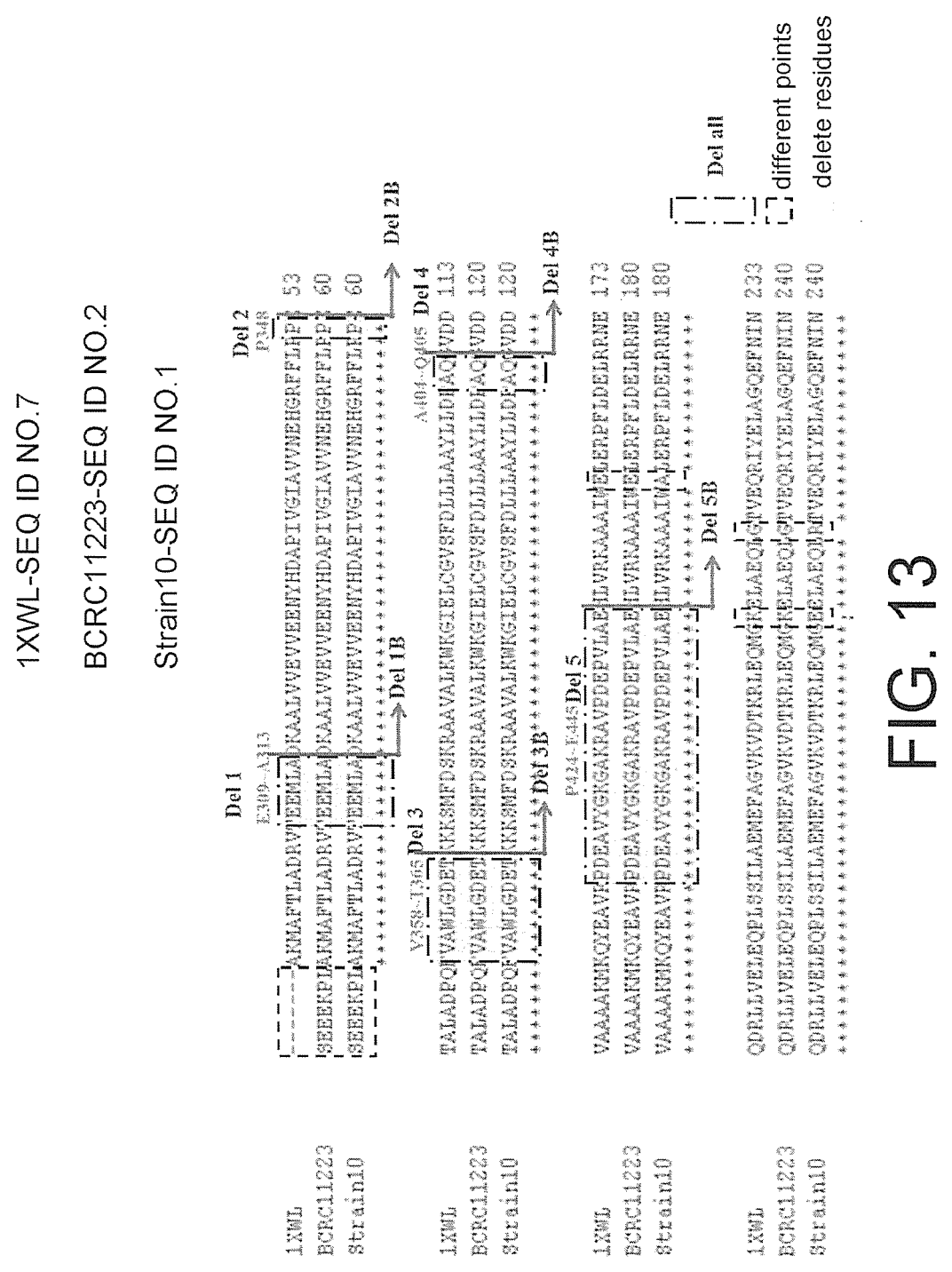

Cloning of Point-Mutation Gene of DNA Polymerase I of *G. Kaustophilus* BCRC11223 and Activity Assay Cloning of Point-Mutation Gene of DNA Polymerase and Enzyme Purification Gene Sequence Analysis According to the simulation analysis aiming at the 3D structures and amino acid sequences of different DNA polymerases, it is speculated that the enzyme structure remains stable after partial removal of the specific sequence. Also, the stability of the enzyme is improved and the storage of the enzyme under the room temperature is satisfactory. Based on the analysis results of the amino acid sequences, it is estimated that five fragments may be deleted from the amino acid sequence(s), which may enhance stability. The commercialized product of Bst DNA polymerase I is the large fragment of the enzyme by removing the fragment of 5'→3' exonuclease domain. The large fragment starts from 289$^{th}$ amino acid residue to the C-terminus. In this experiment, N-terminus amino acid sequence of various lengths as subsections at different positions were deleted to observe whether the stability of the enzyme was enhanced. FIG. 13 shows the deleted fragments of the amino acid sequences of Strain-10, BCRC11223, wherein the deleted fragment (marked as red arrows) may be any of the five deleted fragments, naming after it, the deletion refers to FIG. 13 and the deletion clone is named based on the deleted fragments.

Gene Cloning and Expression of *G. kaustophilus* BCRC11223 polA Deletion Clone

DNA primers PCR reactions were designed toward positions of the deleted amino acids of *G. kaustophilus* BCRC11223 polA gene. After the DNA sequences of the polA large fragment were amplified using the overlap-PCR approach, the sequences were then inserted into the carrier pQE30 (Qiagen Co.) and transfected to *E. coli* host cells for expression. It has successfully selected *E. coli* transformant strains carrying *G. kaustophilus* BCRC11223 polA gene(s), and were named as *E. coli* (pQE-123 del 1), *E. coli* (pQE-123 del 3), *E. coli* (pQE-123 del 4) and *E. coli* (pQE-123 del all), the naming of the deletion clones and the position(s) of the deleted amino acids thereof in reference to FIG. 13. The sequences of the cloned genes were verified as correct sequences by DNA sequencing.

The selected transformant strains of *E. coli* were induced by IPTG to induce T5 promoter of the plasmid for gene expression, and then the bacteria were harvested. The bacteria were washed and redissolved with 20 ml of 50 mM Tris-HCl, pH 8.0, followed by breaking the bacteria using ultrasonic cell disrupter (Ultrasonic processor UP-800, ChromTech, MN, USA), and SDS-PAGE column chromatography was used to evaluate gene expression. The results are as shown in FIGS. 14A-B and 15A-C. In the figures, it showed that *E. coli* transformant strains *E. coli* (pQE-123 del 1), *E. coli* (pQE-123 del 4) and *E. coli* (pQE-123 del 1B) indeed can express a lot of the cloned polA gene, and can express more soluble proteins (columns 1 & 2 of FIG. 14A and columns 1 & 2 of FIGS. 15A & 15B). After purified by Ni$^{2+}$-NTA agar column, the large fragment of DNA polymerase I in high purity was obtained, and the molecular weight of the enzyme is as expected of a size about 65 kDa.

Enzyme Activity Assay of Deletion Clones

The purified enzyme was diluted and stored in the storage buffer (10 mM Tris-HCl pH7.9, 50 mM KCl, 1 mM DTT, 0.1 mM EDTA, 0.1% Triton X-100, 50% glycerol) at −20° C. The enzyme activity assays were as 1.2.2 described previously and the enzyme amount of the commercial available Bst DNA polymerase I (Lucigen Co.) was set to be 0.05 U (16 μg/ml). The amount of the enzyme protein of the purified Bku DNA polymerases from the previously described deletion clones was set to be 16 μg/ml for the activity assay. The total volume of the enzyme reaction was 20 μl. After adding the enzyme, the mixture was reacted at 65° C. for 30 min, 0.8 μl of 0.5M EDTA was added to terminate the reaction. Then, after adding an equal volume of PicoGreen fluorescence dye for reaction at room temperature for 5 minutes, activity analysis was performed. The results are shown in Table 2, 0.05 U of the commercial available Bst DNA polymerase I (Lucigen Co.) can generate 1.29±0.10 μg/ml dsDNA under the reaction conditions of this experiment. However, at the same protein concentration (16 µg/ml), wild-type Bku DNA polymerase can generate 1.42±0.03 µg/ml dsDNA, wherein this activity was used as 100% relative (enzyme) activity. For the deletion clones, under the same reaction conditions, the polymerase mutant Del 1 (the amino acid sequence of Bku DNA polymerase I mutant Del 1 including SEQ ID NO. 3) can generate 1.34±0.10 µg/ml dsDNA, the relative activity of 94.4%, while the polymerase mutant Del 1B of the deletion clone can generate 1.13±0.05 µg/ml dsDNA, the relative activity of 79.6%.

TABLE 3

| Enzyme (0.05 U or 16 µg/ml) | Generated dsDNA (µg/ml) | Relative activity (%)* |
|---|---|---|
| Commercially available Bst DNA polymerase I (Lucigen Co.) | 1.29 ± 0.10 | 90.8 |
| Wild-type Bku DNA polymerase I | 1.42 ± 0.03 | 100.0 |
| Bku DNA polymerase I mutant (Del 1) | 1.34 ± 0.10 | 94.4 |
| Bku DNA polymerase I mutant (Del 3) | 0 | 0 |
| Bku DNA polymerase I mutant (Del 4) | 0.41 ± 0.06 | 29.0 |
| Bku DNA polymerase I mutant (Del 1B) | 1.13 ± 0.05 | 79.6 |

*Relative activity using the activity of wild-type Bku DNA polymerase I as 100%.

Stability Analysis of Deletion Clones

Figure 16:
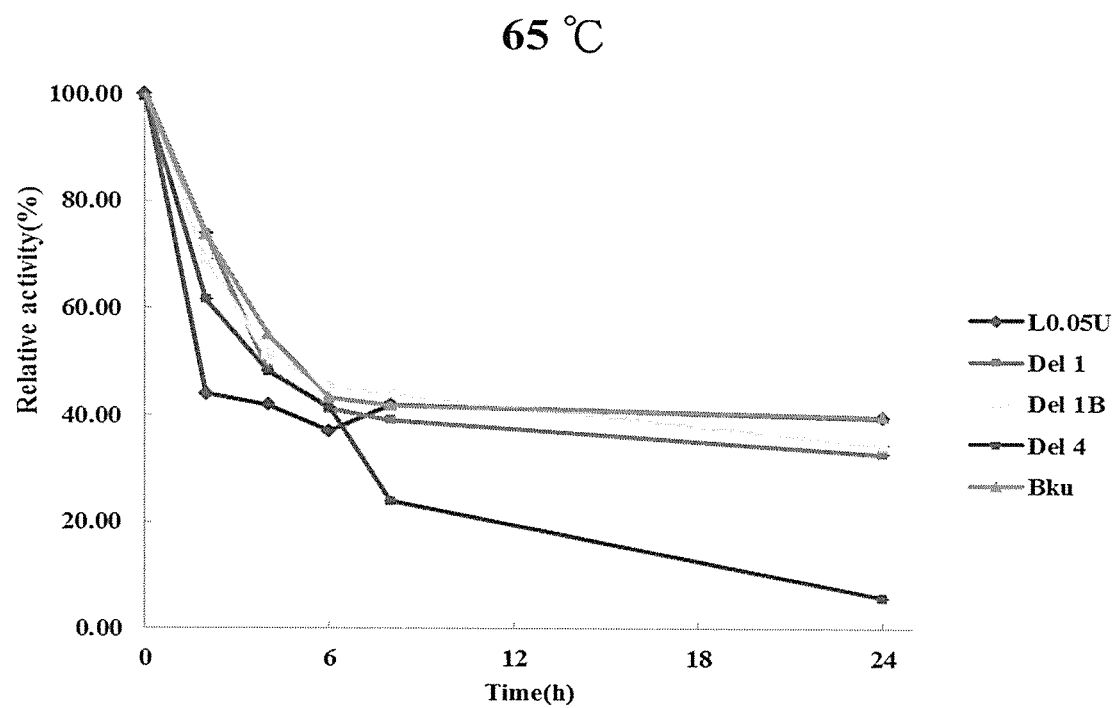
FIG. 16 shows the accelerated storage test results of *Geobacillus* DNA polymerases I from various sources under high temperatures.

The enzymes from the deletion clone were analyzed for stability under the high temperature 65° C. FIG. 16 shows the accelerated storage test results of *Geobacillus* DNA polymerases I from various sources under high temperatures. The results indicated that the relative enzyme activity of the commercially available Bst DNA polymerase I (Lucigen Co.) was lowered to 41% of the original activity after 4 hours. The relative enzyme activity of wild-type Bku DNA polymerase I was lowered to 55% of the original activity after 4 hours. Under the same reaction conditions and over the same period, the relative enzyme activity of the polymerase mutant Del 1B of the deletion clone remained about 51% of the original activity; the relative enzyme activity of the polymerase mutant Del 1 and the polymerase mutant Del 4 remained about 48% of the original activity (referring to FIG. 16). Under the high temperature 65° C. for 8 hours, the relative enzyme activity of the commercially available Bst DNA polymerase I (Lucigen Co.) was lowered to 39% of the original activity. The relative enzyme activity of wild-type Bku DNA polymerase I remained 42% of the original activity. Under the same reaction conditions, the activity of the polymerase mutant Del 1B of the deletion clone was better than those of the commercially available Bst and wild-type Bku DNA polymerases I, 44% of the relative activity remained. The relative enzyme activities of the polymerase mutant Del 1 and the polymerase mutant Del 4 remained to be 39% and 23% (referring to FIG. 16). Based on the results, for the enzyme stability test under the high temperature 65° C., the wild-type Bku DNA polymerase I has a thermostability higher than that of the commercially available Bst DNA polymerase I (Lucigen Co.), and the stability of the polymerase mutant Del 1B of the deletion clone under the high temperature is better than that of the wild-type enzyme.

Figure 17A:
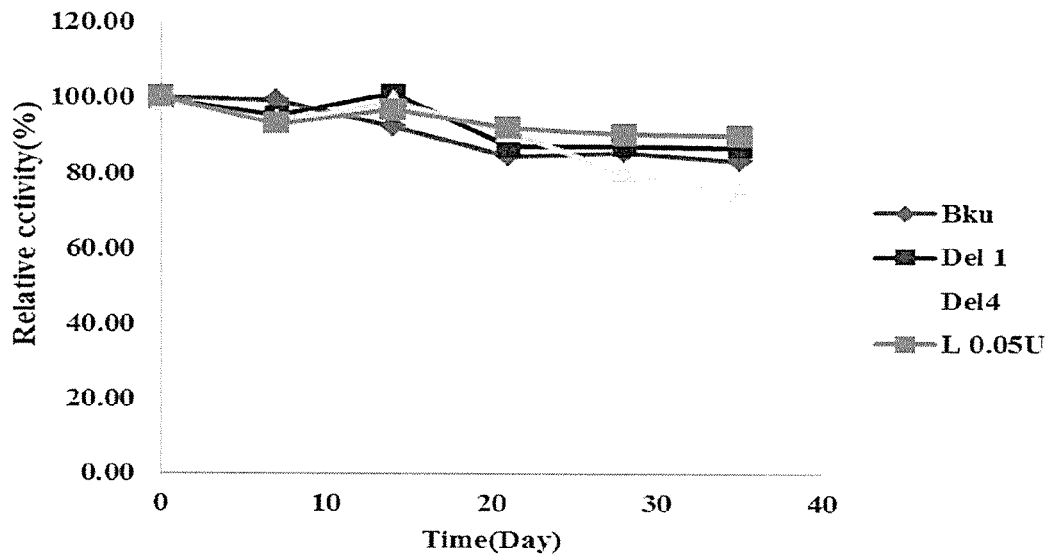
FIG. 17A-C show the stability test results of *Geobacillus* DNA polymerases I from various sources under different temperatures.
Figure 17B:
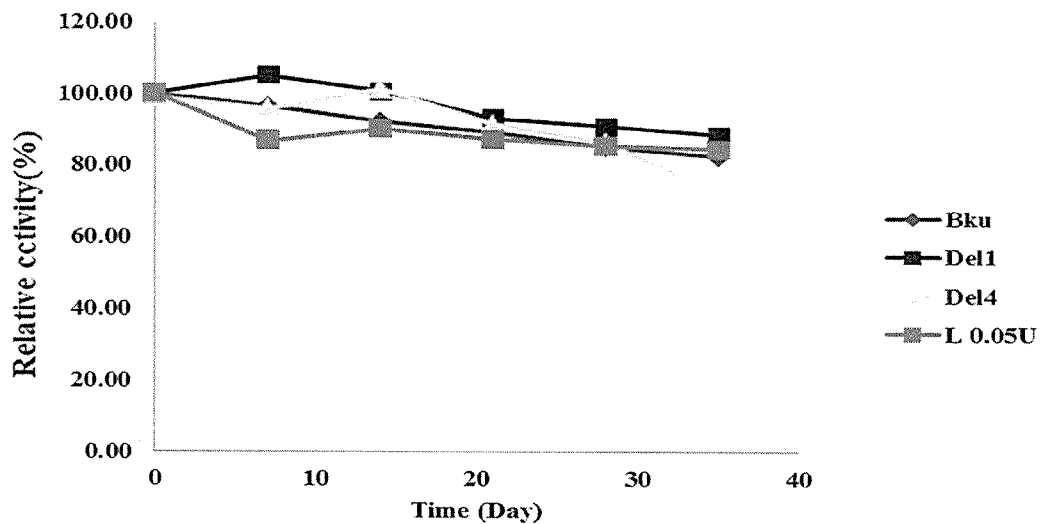
Figure 17C:
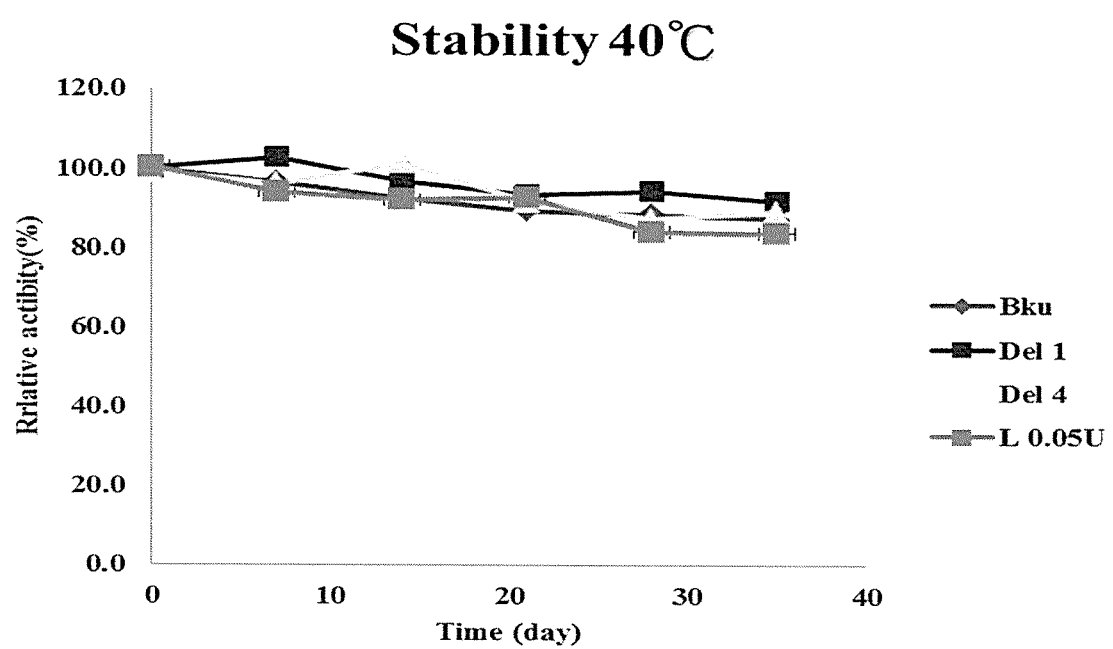

FIG. 17A-C show the stability test results of *Geobacillus* DNA polymerases I from various sources under different temperatures. The storage test under 4° C. lasted for 35 days and the results indicated that the relative enzyme activities of the commercially available Bst DNA polymerase I (Lucigen Co.), Bku DNA polymerase I and the mutant Del 1 remained to be respectively 89%, 83% and 86% of the original activity. The relative enzyme activity of the mutant Del 4 remained 75% of the original activity (referring to FIG. 17A). The results of the storage test under 25° C. showed that after 35 days, the relative enzyme activities of the commercially available Bst DNA polymerase I (Lucigen Co.), Bku DNA polymerase I and the mutant Del 1 remained to be respectively 84%, 83% and 88% of the original activity, while the relative enzyme activity of the mutant Del 4 remained about 73% of the original activity (referring to FIG. 17B). For the storage test under 40° C., after 35 days, the relative enzyme activity of the commercially available Bst DNA polymerase I (Lucigen Co.) was about 83% of the original activity, while the relative enzyme activities of Bku DNA polymerase I, mutant Del 1 and Del 4 remained to be respectively 87%, 91% and 89% of the original activity (referring to FIG. 17C). The results indicated the enzyme stability of Bku DNA polymerase I and the polymerase mutant Del 1 is better than that of the commercially available Bst DNA polymerase I (Lucigen Co.).

The present disclosure provides mutants of an isolated DNA polymerase I, and the isolated DNA polymerase I is Bku DNA polymerase I with the amino acid sequence comprising SEQ ID NO. 2. The mutant has an amino acid sequence by deleting at least one of five fragments from the amino acid sequences in the 3'→5' exonuclease domain of the isolated DNA polymerase. The five fragments are E309-A313, P348, V358-T365, A404-Q405 and P424-E445.

According to the embodiments of this disclosure, the mutant has a thermostability substantially equivalent to that of Bst DNA polymerase I and a strand displacement activity substantially equivalent to that of the Bst DNA polymerase I.

This disclosure also directs to kits or compositions comprising the above mentioned isolated DNA polymerases, mutants or the combinations thereof. The kits may be applicable for polymerase chain reactions (PCR), nucleic acid amplification, whole genome amplification (WGA), multiple displacement amplification (MDA), loop-mediated isothermal amplification (LAMP) and DNA sequencing.

It will be apparent to those skilled in the art that various modifications and variations can be made to the structure of the present disclosure without departing from the scope or spirit of this disclosure. In view of the foregoing, it is intended that the present disclosure cover modifications and variations of this disclosure provided they fall within the scope of the following claims and their equivalents.

What is claimed is:

1. A mutant of an isolated DNA polymerase, consisting of the amino acid sequence of SEQ ID NO. 3.

2. The mutant of claim 1, wherein the mutant has a thermostability substantially equivalent to that of Bst DNA polymerase and a strand displacement activity substantially equivalent to that of the Bst DNA polymerase.

3. A method for nucleic acid amplification reactions, comprises providing the mutant of claim 1 to prepare a nucleic acid amplification reaction composition.

4. The method of claim 3, wherein the nucleic acid amplification reaction comprises polymerase chain reactions (PCR), nucleic acid amplification, whole genome amplification (WGA), multiple displacement amplification (MDA) or DNA sequencing.

5. A kit comprising the mutant of claim 1.

6. The kit of claim 5, wherein the kit is applicable for a nucleic acid amplification reaction.

7. The kit of claim 6, wherein the nucleic acid amplification reaction comprises polymerase chain reactions (PCR), nucleic acid amplification, whole genome amplification (WGA), multiple displacement amplification (MDA) or DNA sequencing.

* * * * *

SEQUENCE LISTING

<160> NUMBER OF SEQ ID NOS: 7

<210> SEQ ID NO 1
<211> LENGTH: 599
<212> TYPE: PRT
<213> ORGANISM: Geobacillus stearothermophilus

<400> SEQUENCE: 1

```
Met Arg Gly Ser His His His His His His Gly Ser Ser Glu Glu Glu
 1               5                  10                  15

Lys Pro Leu Ala Lys Met Ala Phe Thr Leu Ala Asp Arg Val Thr Glu
             20                  25                  30

Glu Met Leu Ala Asp Lys Ala Ala Leu Val Val Glu Val Val Glu Glu
             35                  40              45

Asn Tyr His Asp Ala Pro Ile Val Gly Ile Ala Val Val Asn Glu His
 50                  55                  60

Gly Arg Phe Phe Leu Arg Pro Glu Thr Ala Leu Ala Asp Pro Gln Phe
 65              70                  75                      80

Val Ala Trp Leu Gly Asp Glu Thr Lys Lys Ser Met Phe Asp Ser
                 85                  90                  95

Lys Arg Ala Ala Val Ala Leu Lys Trp Lys Gly Ile Glu Leu Cys Gly
             100                 105                 110

Val Ser Phe Asp Leu Leu Leu Ala Ala Tyr Leu Leu Asp Pro Ala Gln
             115                 120                 125

Gly Val Asp Asp Val Ala Ala Ala Lys Met Lys Gln Tyr Glu Ala
             130                 135             140

Val Arg Pro Asp Glu Ala Val Tyr Gly Lys Gly Ala Lys Arg Ala Val
145                 150                 155                 160

Pro Asp Glu Pro Val Leu Ala Glu His Leu Val Arg Lys Ala Ala
                 165                 170                 175

Ile Trp Ala Leu Glu Arg Pro Phe Leu Asp Glu Leu Arg Arg Asn Glu
             180                 185                 190

Gln Asp Arg Leu Leu Val Glu Leu Glu Gln Pro Leu Ser Ser Ile Leu
             195                 200                 205

Ala Glu Met Glu Phe Ala Gly Val Lys Val Asp Thr Lys Arg Leu Glu
             210                 215                 220

Gln Met Gly Glu Glu Leu Ala Glu Gln Leu Arg Thr Val Glu Gln Arg
225                 230                 235                 240

Ile Tyr Glu Leu Ala Gly Gln Glu Phe Asn Ile Asn Ser Pro Lys Gln
                 245                 250                 255

Leu Gly Val Ile Leu Phe Glu Lys Leu Gln Leu Pro Val Leu Lys Lys
             260                 265                 270

Thr Lys Thr Gly Tyr Ser Thr Ser Ala Asp Val Leu Glu Lys Leu Ala
             275                 280                 285

Pro Tyr His Glu Ile Val Glu Asn Ile Leu His Tyr Arg Gln Leu Gly
             290                 295                 300

Lys Leu Gln Ser Thr Tyr Ile Glu Gly Leu Leu Lys Val Val Arg Pro
305                 310                 315                 320

Asp Thr Lys Lys Val His Thr Ile Phe Asn Gln Ala Leu Thr Gln Thr
                 325                 330                 335

Gly Arg Leu Ser Ser Thr Glu Pro Asn Leu Gln Asn Ile Pro Ile Arg
             340                 345                 350

Leu Glu Glu Gly Arg Lys Ile Arg Gln Ala Phe Val Pro Ser Glu Ser
             355                 360                 365

Asp Trp Leu Ile Phe Ala Ala Asp Tyr Ser Gln Ile Glu Leu Arg Val
             370                 375                 380

Leu Ala His Ile Ala Glu Asp Asp Asn Leu Met Glu Ala Phe Arg Arg
385                 390                 395                 400

Asp Leu Asp Ile His Thr Lys Thr Ala Met Asp Ile Phe Gln Val Ser
                 405                 410                 415

Glu Asp Glu Val Thr Pro Asn Met Arg Arg Gln Ala Lys Ala Val Asn
```

```
                420             425             430
Phe Gly Ile Val Tyr Gly Ile Ser Asp Tyr Gly Leu Ala Gln Asn Leu
            435                 440                 445

Asn Ile Ser Arg Lys Glu Ala Ala Glu Phe Ile Glu Arg Tyr Phe Glu
        450                 455                 460

Ser Phe Pro Gly Val Lys Arg Tyr Met Glu Asn Ile Val Gln Glu Ala
465                 470                 475                 480

Lys Gln Lys Gly Tyr Val Thr Thr Leu Leu His Arg Arg Arg Tyr Leu
                485                 490                 495

Pro Asp Ile Thr Ser Arg Asn Phe Asn Val Arg Ser Phe Ala Glu Arg
            500                 505                 510

Met Ala Met Asn Thr Pro Ile Gln Gly Ser Ala Ala Asp Ile Ile Lys
        515                 520                 525

Lys Ala Met Ile Asp Leu Asn Ala Arg Leu Lys Glu Glu Arg Leu Gln
530                 535                 540

Ala Arg Leu Leu Leu Gln Val His Asp Glu Leu Ile Leu Glu Ala Pro
545                 550                 555                 560

Lys Glu Glu Met Glu Arg Leu Cys Arg Leu Val Pro Glu Val Met Glu
                565                 570                 575

Gln Ala Val Thr Leu Arg Val Pro Leu Lys Val Asp Tyr His Tyr Gly
            580                 585                 590

Ser Thr Trp Tyr Asp Ala Lys
            595

<210> SEQ ID NO 2
<211> LENGTH: 599
<212> TYPE: PRT
<213> ORGANISM: Geobacillus kaustophilus

<400> SEQUENCE: 2

Met Arg Gly Ser His His His His His His Gly Ser Glu Glu Glu
1               5                   10                  15

Lys Pro Leu Ala Lys Met Ala Phe Thr Leu Ala Asp Arg Val Thr Glu
            20                  25                  30

Glu Met Leu Ala Asp Lys Ala Ala Leu Val Val Glu Val Val Glu Glu
        35                  40                  45

Asn Tyr His Asp Ala Pro Ile Val Gly Ile Ala Val Val Asn Glu His
    50                  55                  60

Gly Arg Phe Phe Leu Arg Pro Glu Thr Ala Leu Ala Asp Pro Gln Phe
65                  70                  75                  80

Val Ala Trp Leu Gly Asp Glu Thr Lys Lys Lys Ser Met Phe Asp Ser
                85                  90                  95

Lys Arg Ala Ala Val Ala Leu Lys Trp Lys Gly Ile Glu Leu Cys Gly
            100                 105                 110

Val Ser Phe Asp Leu Leu Leu Ala Ala Tyr Leu Leu Asp Pro Ala Gln
        115                 120                 125

Gly Val Asp Asp Val Ala Ala Ala Lys Met Lys Gln Tyr Glu Ala
            130                 135                 140

Val Arg Pro Asp Glu Ala Val Tyr Gly Lys Gly Ala Lys Arg Ala Val
145                 150                 155                 160

Pro Asp Glu Pro Val Leu Ala Glu His Leu Val Arg Lys Ala Ala Ala
                165                 170                 175

Ile Trp Glu Leu Glu Arg Pro Phe Leu Asp Glu Leu Arg Arg Asn Glu
            180                 185                 190
```

```
Gln Asp Arg Leu Leu Val Glu Leu Glu Gln Pro Leu Ser Ser Ile Leu
        195                 200                 205

Ala Glu Met Glu Phe Ala Gly Val Lys Val Asp Thr Lys Arg Leu Glu
210                 215                 220

Gln Met Gly Lys Glu Leu Ala Glu Gln Leu Gly Thr Val Glu Gln Arg
225                 230                 235                 240

Ile Tyr Glu Leu Ala Gly Gln Glu Phe Asn Ile Asn Ser Pro Lys Gln
                245                 250                 255

Leu Gly Val Ile Leu Phe Glu Lys Leu Gln Leu Pro Val Leu Lys Lys
                260                 265                 270

Thr Lys Thr Gly Tyr Ser Thr Ser Ala Asp Val Leu Glu Lys Leu Ala
                275                 280                 285

Pro Tyr His Glu Ile Val Glu Asn Ile Leu His Tyr Arg Gln Leu Gly
            290                 295                 300

Lys Leu Gln Ser Thr Tyr Ile Glu Gly Leu Leu Lys Val Val Arg Pro
305                 310                 315                 320

Asp Thr Lys Lys Val His Thr Ile Phe Asn Gln Ala Leu Thr Gln Thr
                325                 330                 335

Gly Arg Leu Ser Ser Thr Glu Pro Asn Leu Gln Asn Ile Pro Ile Arg
                340                 345                 350

Leu Glu Glu Gly Arg Lys Ile Arg Gln Ala Phe Val Pro Ser Glu Ser
            355                 360                 365

Asp Trp Leu Ile Phe Ala Ala Asp Tyr Ser Gln Ile Glu Leu Arg Val
            370                 375                 380

Leu Ala His Ile Ala Glu Asp Asp Asn Leu Met Glu Ala Phe Arg Arg
385                 390                 395                 400

Asp Leu Asp Ile His Thr Lys Thr Ala Met Asp Ile Phe Gln Val Ser
                405                 410                 415

Glu Asp Glu Val Thr Pro Asn Met Arg Arg Gln Ala Lys Ala Val Asn
                420                 425                 430

Phe Gly Ile Val Tyr Gly Ile Ser Asp Tyr Gly Leu Ala Gln Asn Leu
            435                 440                 445

Asn Ile Ser Arg Lys Glu Ala Ala Glu Phe Ile Glu Arg Tyr Phe Glu
            450                 455                 460

Ser Phe Pro Gly Val Lys Arg Tyr Met Glu Asn Ile Val Gln Glu Ala
465                 470                 475                 480

Lys Gln Lys Gly Tyr Val Thr Thr Leu Leu His Arg Arg Arg Tyr Leu
                485                 490                 495

Pro Asp Ile Thr Ser Arg Asn Phe Asn Val Arg Ser Phe Ala Glu Arg
            500                 505                 510

Met Ala Met Asn Thr Pro Ile Gln Gly Ser Ala Ala Asp Ile Ile Lys
            515                 520                 525

Lys Ala Met Ile Asp Leu Asn Ala Arg Leu Lys Glu Glu Arg Leu Gln
530                 535                 540

Ala Arg Leu Leu Leu Gln Val His Asp Glu Leu Ile Leu Glu Ala Pro
545                 550                 555                 560

Lys Glu Glu Met Glu Arg Leu Cys Arg Leu Val Pro Glu Val Met Glu
                565                 570                 575

Gln Ala Val Thr Leu Arg Val Pro Leu Lys Val Asp Tyr His Tyr Gly
                580                 585                 590

Ser Thr Trp Tyr Asp Ala Lys
            595
```

```
<210> SEQ ID NO 3
<211> LENGTH: 594
<212> TYPE: PRT
<213> ORGANISM: Geobacillus kaustophilus

<400> SEQUENCE: 3

Met Arg Gly Ser His His His His His His Gly Ser Ser Glu Glu
1               5                   10                  15

Lys Pro Leu Ala Lys Met Ala Phe Thr Leu Ala Asp Arg Val Thr Asp
            20                  25                  30

Lys Ala Ala Leu Val Val Glu Val Val Glu Glu Asn Tyr His Asp Ala
            35                  40                  45

Pro Ile Val Gly Ile Ala Val Val Asn Glu His Gly Arg Phe Phe Leu
50                  55                  60

Arg Pro Glu Thr Ala Leu Ala Asp Pro Gln Phe Val Ala Trp Leu Gly
65                  70                  75                  80

Asp Glu Thr Lys Lys Lys Ser Met Phe Asp Ser Lys Arg Ala Ala Val
                85                  90                  95

Ala Leu Lys Trp Lys Gly Ile Glu Leu Cys Gly Val Ser Phe Asp Leu
            100                 105                 110

Leu Leu Ala Ala Tyr Leu Leu Asp Pro Ala Gln Gly Val Asp Asp Val
            115                 120                 125

Ala Ala Ala Ala Lys Met Lys Gln Tyr Glu Ala Val Arg Pro Asp Glu
130                 135                 140

Ala Val Tyr Gly Lys Gly Ala Lys Arg Ala Val Pro Asp Glu Pro Val
145                 150                 155                 160

Leu Ala Glu His Leu Val Arg Lys Ala Ala Ile Trp Glu Leu Glu
            165                 170                 175

Arg Pro Phe Leu Asp Glu Leu Arg Arg Asn Glu Gln Asp Arg Leu Leu
            180                 185                 190

Val Glu Leu Glu Gln Pro Leu Ser Ser Ile Leu Ala Glu Met Glu Phe
            195                 200                 205

Ala Gly Val Lys Val Asp Thr Lys Arg Leu Glu Gln Met Gly Lys Glu
210                 215                 220

Leu Ala Glu Gln Leu Gly Thr Val Glu Gln Arg Ile Tyr Glu Leu Ala
225                 230                 235                 240

Gly Gln Glu Phe Asn Ile Asn Ser Pro Lys Gln Leu Gly Val Ile Leu
                245                 250                 255

Phe Glu Lys Leu Gln Leu Pro Val Leu Lys Lys Thr Lys Thr Gly Tyr
            260                 265                 270

Ser Thr Ser Ala Asp Val Leu Glu Lys Leu Ala Pro Tyr His Glu Ile
            275                 280                 285

Val Glu Asn Ile Leu His Tyr Arg Gln Leu Gly Lys Leu Gln Ser Thr
290                 295                 300

Tyr Ile Glu Gly Leu Leu Lys Val Val Arg Pro Asp Thr Lys Lys Val
305                 310                 315                 320

His Thr Ile Phe Asn Gln Ala Leu Thr Gln Thr Gly Arg Leu Ser Ser
                325                 330                 335

Thr Glu Pro Asn Leu Gln Asn Ile Pro Ile Arg Leu Glu Glu Gly Arg
            340                 345                 350

Lys Ile Arg Gln Ala Phe Val Pro Ser Glu Ser Asp Trp Leu Ile Phe
            355                 360                 365

Ala Ala Asp Tyr Ser Gln Ile Glu Leu Arg Val Leu Ala His Ile Ala
370                 375                 380
```

```
Glu Asp Asp Asn Leu Met Glu Ala Phe Arg Arg Asp Leu Asp Ile His
385                 390                 395                 400

Thr Lys Thr Ala Met Asp Ile Phe Gln Val Ser Glu Asp Glu Val Thr
            405                 410                 415

Pro Asn Met Arg Arg Gln Ala Lys Ala Val Asn Phe Gly Ile Val Tyr
        420                 425                 430

Gly Ile Ser Asp Tyr Gly Leu Ala Gln Asn Leu Asn Ile Ser Arg Lys
        435                 440                 445

Glu Ala Glu Phe Ile Glu Arg Tyr Phe Glu Ser Phe Pro Gly Val
    450                 455                 460

Lys Arg Tyr Met Glu Asn Ile Val Gln Glu Ala Lys Gln Lys Gly Tyr
465                 470                 475                 480

Val Thr Thr Leu Leu His Arg Arg Tyr Leu Pro Asp Ile Thr Ser
            485                 490                 495

Arg Asn Phe Asn Val Arg Ser Phe Ala Glu Arg Met Ala Met Asn Thr
                500                 505                 510

Pro Ile Gln Gly Ser Ala Ala Asp Ile Ile Lys Lys Ala Met Ile Asp
            515                 520                 525

Leu Asn Ala Arg Leu Lys Glu Glu Arg Leu Gln Ala Arg Leu Leu Leu
        530                 535                 540

Gln Val His Asp Glu Leu Ile Leu Glu Ala Pro Lys Glu Glu Met Glu
545                 550                 555                 560

Arg Leu Cys Arg Leu Val Pro Glu Val Met Glu Gln Ala Val Thr Leu
                565                 570                 575

Arg Val Pro Leu Lys Val Asp Tyr His Tyr Gly Ser Thr Trp Tyr Asp
            580                 585                 590

Ala Lys

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
gaggatcctc agaagaggaa aaaccgct                                      28

<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
gaggtacctt atttcgcatc ataccacg                                      28

<210> SEQ ID NO 6
<211> LENGTH: 35
<212> TYPE: DNA
<213> ORGANISM: Artificial Sequence
<220> FEATURE:
<223> OTHER INFORMATION: UP primer

<400> SEQUENCE: 6
ttcccagtca cgacgttgta aaacgacggc cagtg                              35

<210> SEQ ID NO 7
```

<211> LENGTH: 580
<212> TYPE: PRT
<213> ORGANISM: Bacillus stearothermophilus

<400> SEQUENCE: 7

```
Ala Lys Met Ala Phe Thr Leu Ala Asp Arg Val Thr Glu Glu Met Leu
1               5                   10                  15

Ala Asp Lys Ala Ala Leu Val Val Glu Val Val Glu Glu Asn Tyr His
                20                  25                  30

Asp Ala Pro Ile Val Gly Ile Ala Val Val Asn Glu His Gly Arg Phe
            35                  40                  45

Phe Leu Arg Pro Glu Thr Ala Leu Ala Asp Pro Gln Phe Val Ala Trp
        50                  55                  60

Leu Gly Asp Glu Thr Lys Lys Ser Met Phe Asp Ser Lys Arg Ala
65                  70                  75                  80

Ala Val Ala Leu Lys Trp Lys Gly Ile Glu Leu Cys Gly Val Ser Phe
                85                  90                  95

Asp Leu Leu Leu Ala Ala Tyr Leu Leu Asp Pro Ala Gln Gly Val Asp
            100                 105                 110

Asp Val Ala Ala Ala Lys Met Lys Gln Tyr Glu Ala Val Arg Pro
        115                 120                 125

Asp Glu Ala Val Tyr Gly Lys Gly Ala Lys Arg Ala Val Pro Asp Glu
130                 135                 140

Pro Val Leu Ala Glu His Leu Val Arg Lys Ala Ala Ile Trp Glu
145                 150                 155                 160

Leu Glu Arg Pro Phe Leu Asp Glu Leu Arg Arg Asn Glu Gln Asp Arg
                165                 170                 175

Leu Leu Val Glu Leu Glu Gln Pro Leu Ser Ser Ile Leu Ala Glu Met
            180                 185                 190

Glu Phe Ala Gly Val Lys Val Asp Thr Lys Arg Leu Glu Gln Met Gly
        195                 200                 205

Lys Glu Leu Ala Glu Gln Leu Gly Thr Val Glu Gln Arg Ile Tyr Glu
    210                 215                 220

Leu Ala Gly Gln Glu Phe Asn Ile Asn Ser Pro Lys Gln Leu Gly Val
225                 230                 235                 240

Ile Leu Phe Glu Lys Leu Gln Leu Pro Val Leu Lys Lys Thr Lys Thr
                245                 250                 255

Gly Tyr Ser Thr Ser Ala Asp Val Leu Glu Lys Leu Ala Pro Tyr His
            260                 265                 270

Glu Ile Val Glu Asn Ile Leu His Tyr Arg Gln Leu Gly Lys Leu Gln
        275                 280                 285

Ser Thr Tyr Ile Glu Gly Leu Leu Lys Val Val Arg Pro Asp Thr Lys
    290                 295                 300

Lys Val His Thr Ile Phe Asn Gln Ala Leu Thr Gln Thr Gly Arg Leu
305                 310                 315                 320

Ser Ser Thr Glu Pro Asn Leu Gln Asn Ile Pro Ile Arg Leu Glu Glu
                325                 330                 335

Gly Arg Lys Ile Arg Gln Ala Phe Val Pro Ser Glu Ser Asp Trp Leu
            340                 345                 350

Ile Phe Ala Ala Asp Tyr Ser Gln Ile Glu Leu Arg Val Leu Ala His
        355                 360                 365

Ile Ala Glu Asp Asp Asn Leu Met Glu Ala Phe Arg Arg Asp Leu Asp
    370                 375                 380

Ile His Thr Lys Thr Ala Met Asp Ile Phe Gln Val Ser Glu Asp Glu
```

-continued

```
385                 390                 395                 400

Val Thr Pro Asn Met Arg Arg Gln Ala Lys Ala Val Asn Phe Gly Ile
            405                 410                 415

Val Tyr Gly Ile Ser Asp Tyr Gly Leu Ala Gln Asn Leu Asn Ile Ser
            420                 425                 430

Arg Lys Glu Ala Ala Glu Phe Ile Glu Arg Tyr Phe Glu Ser Phe Pro
        435                 440                 445

Gly Val Lys Arg Tyr Met Glu Asn Ile Val Gln Glu Ala Lys Gln Lys
        450                 455                 460

Gly Tyr Val Thr Thr Leu Leu His Arg Arg Arg Tyr Leu Pro Asp Ile
465                 470                 475                 480

Thr Ser Arg Asn Phe Asn Val Arg Ser Phe Ala Glu Arg Met Ala Met
            485                 490                 495

Asn Thr Pro Ile Gln Gly Ser Ala Ala Asp Ile Ile Lys Lys Ala Met
            500                 505                 510

Ile Asp Leu Asn Ala Arg Leu Lys Glu Glu Arg Leu Gln Ala His Leu
            515                 520                 525

Leu Leu Gln Val His Asp Glu Leu Ile Leu Glu Ala Pro Lys Glu Glu
        530                 535                 540

Met Glu Arg Leu Cys Arg Leu Val Pro Glu Val Met Glu Gln Ala Val
545                 550                 555                 560

Thr Leu Arg Val Pro Leu Lys Val Asp Tyr His Tyr Gly Ser Thr Trp
            565                 570                 575

Tyr Asp Ala Lys
            580
```